(12) United States Patent
Kalofolias

(10) Patent No.: US 10,485,733 B2
(45) Date of Patent: Nov. 26, 2019

(54) DEVICES AND METHODS FOR ESTABLISHING COMMUNICATION BETWEEN CHAMBERS IN A MULTI-CHAMBERED VESSEL

(71) Applicant: Cube Pharmaceuticals N. Kalofolias & Co., Athens (GR)

(72) Inventor: Evagelos Kalofolias, Marousi (GR)

(73) Assignee: Cube Pharmaceuticals N. Kalofolias & Co., Athens (GR)

(*) Notice: Subject to any disclaimer, the term of this patent is extended or adjusted under 35 U.S.C. 154(b) by 0 days.

(21) Appl. No.: 15/662,889

(22) Filed: Jul. 28, 2017

(65) Prior Publication Data

US 2018/0333331 A1 Nov. 22, 2018

Related U.S. Application Data

(63) Continuation of application No. PCT/EP2016/051711, filed on Jan. 27, 2016.

(30) Foreign Application Priority Data

Jan. 28, 2015 (GR) .............................. 20150100029

(51) Int. Cl.
*A61J 1/20* (2006.01)
*A61M 5/19* (2006.01)
(Continued)

(52) U.S. Cl.
CPC ............ *A61J 1/2093* (2013.01); *A45D 34/04* (2013.01); *A61J 1/2072* (2015.05); *A61M 5/19* (2013.01);
(Continued)

(58) Field of Classification Search
CPC ....... A61J 1/2093; A61J 1/2072; B65B 3/003; B01F 15/0237; B01F 15/0087;
(Continued)

(56) References Cited

U.S. PATENT DOCUMENTS

| 4,439,184 A | 3/1984 | Wheeler |
| 2012/0305519 A1 | 12/2012 | Lee et al. |
| 2018/0064874 A1 | 3/2018 | Kalofolias |

FOREIGN PATENT DOCUMENTS

| GB | 1300163 A | 3/1970 |
| JP | H0775673 A | 3/1995 |

(Continued)

OTHER PUBLICATIONS

Bormioli Rocco Pharma, "Biphase Kit", Bormioli Rocco Packaging, http://www.bormioliroccopackaging.com/en/pharma/single-dose/powerrec/powerrec/biphase-kit.html, retrieved online Nov. 6, 2017.

(Continued)

*Primary Examiner* — Leslie R Deak
(74) *Attorney, Agent, or Firm* — Elmore Patent Law Group, P.C.; Carolyn Elmore; Mahreen Hoda

(57) ABSTRACT

The present invention relates in part to vessels comprising a first chamber a second chamber and a seal separating the first and second chambers. In particular, the invention concerns means and methods for establishing communication between the first chamber and a second chamber of such vessels. Vessels of the invention may comprise one or more projections on an internal wall of the vessel and an actuator configured to cause the seal and the one or more projections to engage one another. The one or more projections are configured to urge a portion of the seal away from the internal wall upon engagement with the seal. This causes one or more channels to open between the first chamber and the second chamber. Vessels of the invention allow a user to establish communication between the first chamber and the second chamber at a desired time, for example in order to contact components contained within the chambers or in order to sequentially release components or doses of components from the vessel.

14 Claims, 14 Drawing Sheets

(51) Int. Cl.
   *A61M 5/20* (2006.01)
   *A61M 5/28* (2006.01)
   *A45D 34/04* (2006.01)
   *A61M 5/31* (2006.01)
   *B01F 15/00* (2006.01)
   *B01F 15/02* (2006.01)
   *B65B 3/00* (2006.01)
   *A61M 5/178* (2006.01)
   *A45D 34/00* (2006.01)

(52) U.S. Cl.
   CPC .......... *A61M 5/2066* (2013.01); *A61M 5/284* (2013.01); *A61M 5/3129* (2013.01); *B01F 15/0087* (2013.01); *B01F 15/0237* (2013.01); *B65B 3/003* (2013.01); *A45D 2034/005* (2013.01); *A45D 2200/055* (2013.01); *A61M 2005/1787* (2013.01); *A61M 2005/3114* (2013.01); *A61M 2005/3132* (2013.01); *B01F 2215/0034* (2013.01)

(58) Field of Classification Search
   CPC ......... B01F 2215/0034; A61M 5/3129; A61M 5/2066; A61M 5/19; A61M 5/284; A61M 2005/3114; A61M 2005/1787; A61M 2005/3132; A45D 34/04; A45D 2034/005; A45D 2200/055
   See application file for complete search history.

(56) References Cited

FOREIGN PATENT DOCUMENTS

| | | |
|---|---|---|
| JP | H119692 A | 1/1999 |
| JP | 2011245284 A | 12/2011 |
| WO | 9736624 A1 | 10/1997 |

OTHER PUBLICATIONS

VICAP Systems, "The Caps", http://www.vicapsystems.eu/products/caps/, retrieved online Nov. 6, 2017.

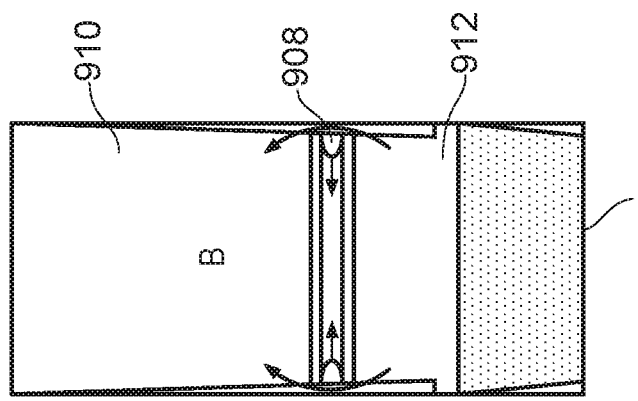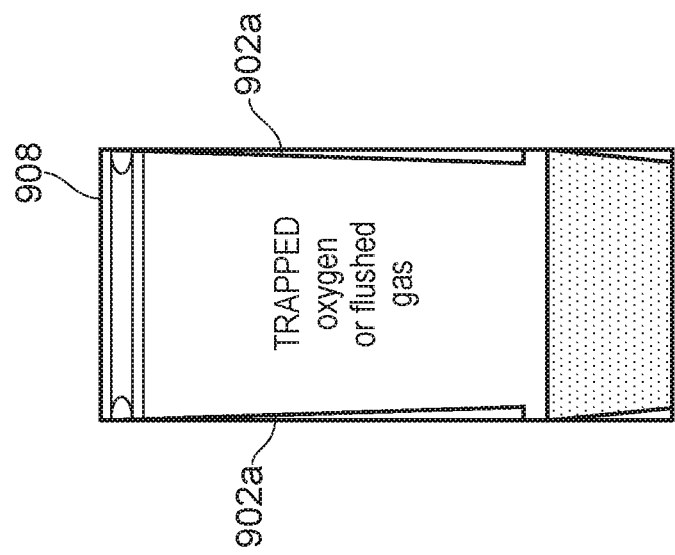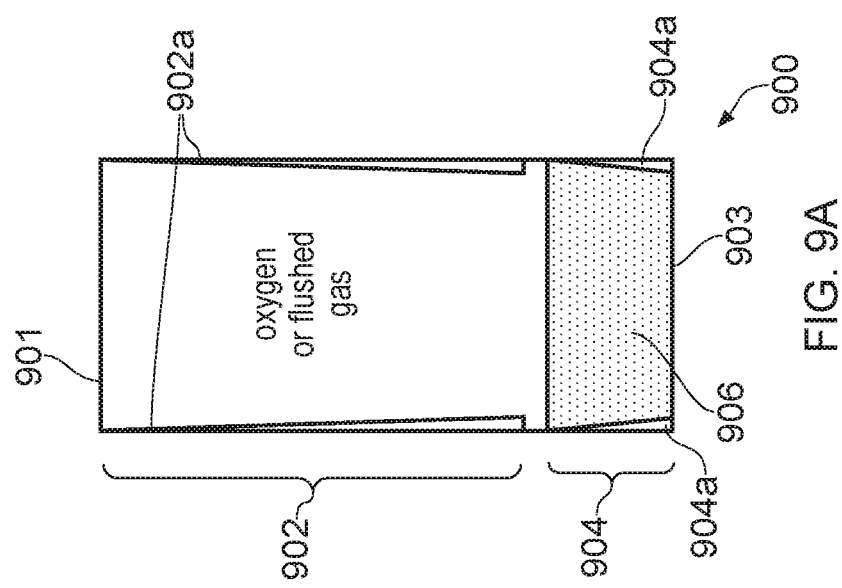

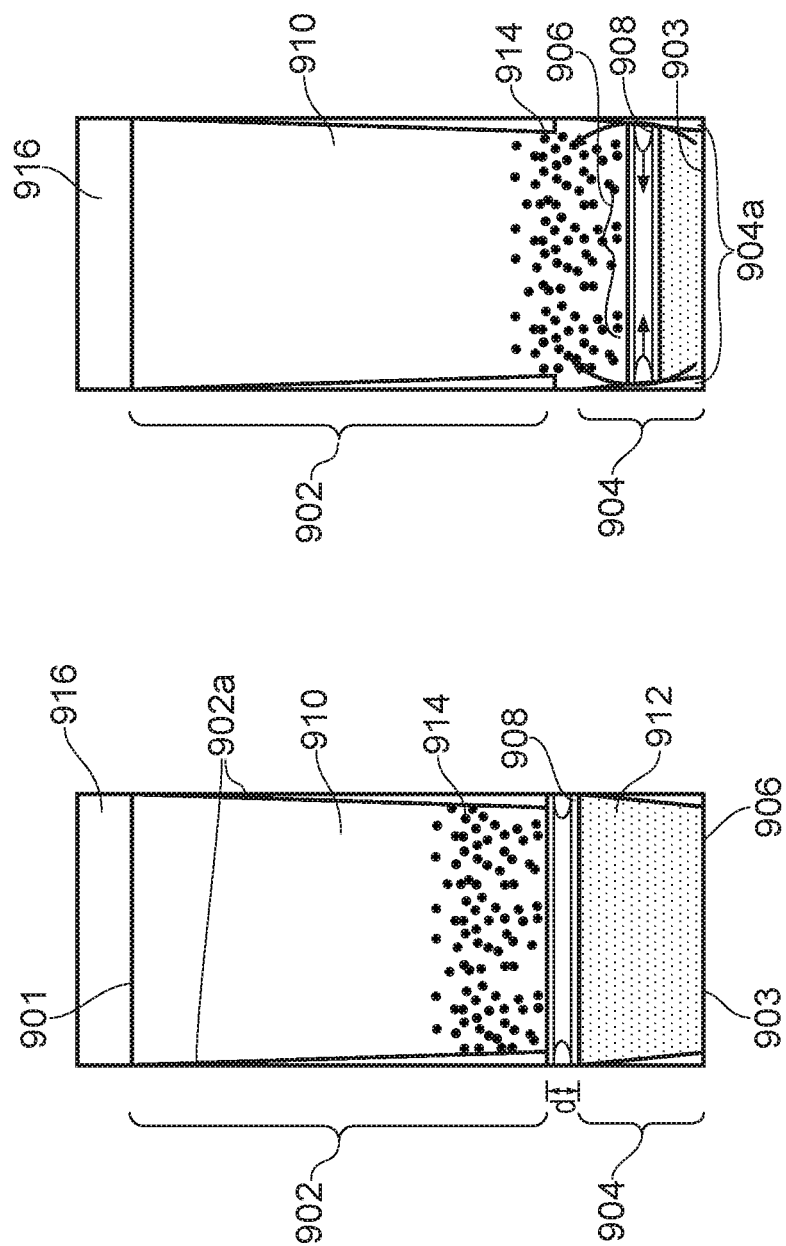

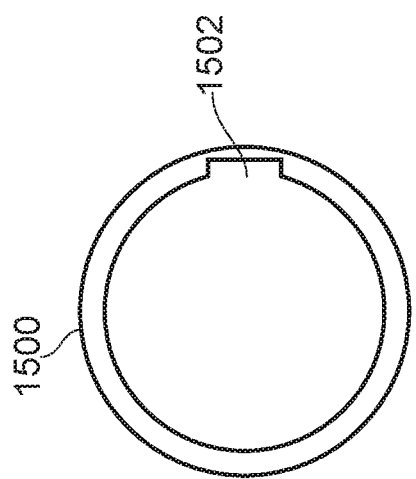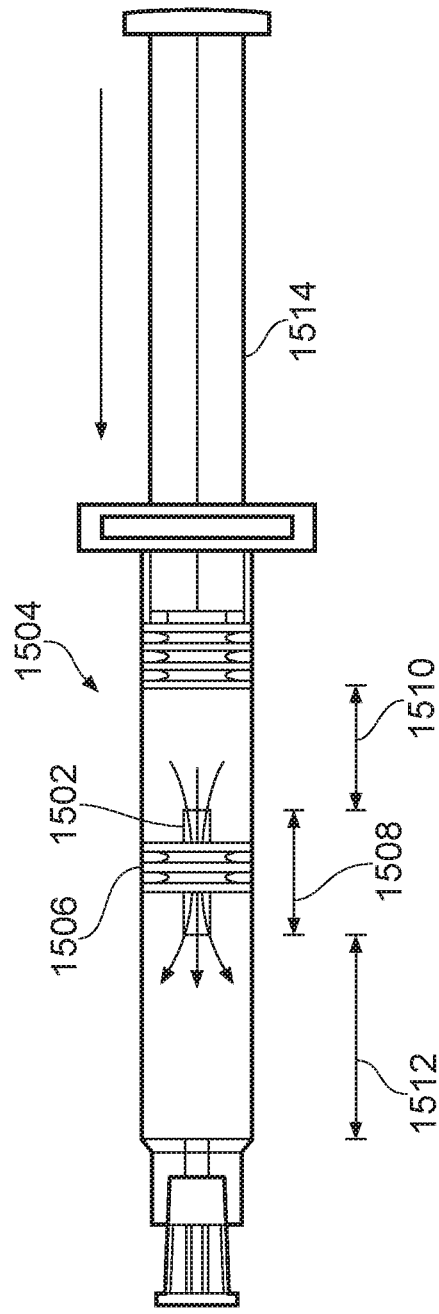
FIG. 15A
FIG. 15B

DEVICES AND METHODS FOR ESTABLISHING COMMUNICATION BETWEEN CHAMBERS IN A MULTI-CHAMBERED VESSEL

RELATED APPLICATIONS

This application is a continuation of PCT/EP2016/051711, filed Jan. 27, 2016, which claims priority under 35 U.S.C. § 119 or 365 to Greek Application No. 20150100029, filed Jan. 28, 2015. The entire teachings of the above applications are incorporated herein by reference.

BACKGROUND

In recent years, the popularity of lyophilised drugs has risen and has been accompanied by the development of prefilled syringes, pre-filled dual-chambered syringes and dual chambered cartridges for their administration. This has been driven by the market's need for means to facilitate reconstitution of such drugs, increase dose accuracy, avoid dosing and reconstitution mistakes, and improve patient safety and compliance, particularly in the case of self-administered products.

As no filling, measuring or mixing outside the syringe is required by a user, such syringes are convenient and safe to use and allow rapid administration of drugs, making them ideal for self-administration.

Such prefilled syringes/cartridges typically contain a measured dose of a lyophilised drug, in a first chamber, and a diluent in a second chamber. The two chambers are separated by a movable seal. The diameter of the seal is equal to the internal diameter of the second chamber. On application of pressure to a plunger, the seal is forced longitudinally through the second chamber until it reaches a bulge in the wall of the syringe. The diameter of the seal is less than the diameter of the bulged portion of the syringe such that, when the seal reaches the bulged portion, a channel is formed between the seal and the wall allowing diluent to bypass the seal and enter the first chamber to contact the drug. The drug can then be dissolved in the diluent and administered in the normal manner.

It would be desirable to provide an alternative vessel that can control communication between a first chamber and a second chamber that does not require a bulged wall portion. This is because forming the bulged wall adds complexity to the manufacturing process and may affect the structural integrity of the vessel. It would also be advantageous to be able to convert a regular syringe into a dual-chambered syringe which can control communication between the two chambers. A further problem associated with existing dual chambered syringes is the opportunity for components to become trapped in the bypass portion of the device and/or flow back into the first chamber once mixed. This may require the user to further manipulate the device (e.g. angle) in order to ensure that the components are properly combined and that the full dose is administered, which is inconvenient. It would also be advantageous to be able to convert a regular syringe into a dual-chambered syringe which can control communication between the two chambers.

An alternative approach to a dual-chambered vessel capable of keeping components separate until a desired time are dispenser caps of the type used in the health, cosmetics, nutrition and beverage industries as well as in the sports drinks field. An example of a cap used in the sports drink field is available from Vicap Systems EMEA Ltd, Switzerland. A first component is contained in a specialised bottle cap comprising a closure system. The closure system includes a barrier separating the first component from the contents of a bottle to which the cap is fitted, and a puncture device. The puncture device can be operated to puncture the barrier allowing delivery of the first component into the bottle. Further details can be found at the following URL: http://www.vicapsystems.eu/products/caps/. Another example of a dispenser cap is a Biphase Cap available from Bormioli Rocco S.p.A., Italy. Further details can be found at the following URL: http://www.bormioliroccopackaging-.com/en/pharma/single-dose/traditional/traditional/biphase-kit.html.

Problems with the dispenser cap approach are that the capacity and dimensions of the caps are restricted by the dimensions of the bottle or vial (particularly the neck) to which the cap is fitted, which are typically a standard size or very market/cost needs oriented. The dispenser cap is also restricted by the way in which standard caps are designed to engage the neck of standard bottles or vials (screw neck, crimp neck). The cap is also limited in terms of providing a stable environment for components because of the chemical structure (material) of the cap, the number of parts used for creating the cap and the sealing process in general, which make it difficult to achieve a hermetically sealed environment.

SUMMARY OF THE INVENTION

In a first aspect, the invention provides a vessel having a proximal end and a distal end and comprising
  a removable seal for defining first and second chambers within the vessel,
  a proximal bypass zone comprising one or more proximal projections on an internal wall of the vessel,
  a distal bypass zone comprising one or more distal projections on an internal wall of the vessel, and
  an actuator configured to move the seal through the vessel and cause the seal to engage the one or more proximal projections and the one or more distal projections,
  wherein the proximal and distal projections are configured to urge a portion of the seal away from the internal wall of the vessel upon engagement with the seal thereby opening one or more channels which bypass the seal, and
  wherein the proximal bypass zone and the distal bypass zone are separated by a distance that is greater than or equal to the thickness of the seal.

As the proximal bypass zone and the distal bypass zone are separated by a distance that is greater than or equal to the thickness of the seal, the seal can be positioned between the proximal and distal bypass zones at a sealing position. In this sealing position, the seal does not engage any of the projections and therefore can prevent fluid (or flowable solid) communication between first and second chambers on either side of the seal.

One particular advantage of such a vessel is that it allows a user to partially fill the vessel with a first component, insert a seal to define a first chamber containing the first component, remove air or other gas from the first chamber, introduce a second component into the vessel on the opposing side of the seal to the first component, and, at a desired time, contact the first and second components. This process will now be explained in more detail with reference to a vessel according to one embodiment of the invention.

A first component may be introduced into the vessel via an opening, which may, for example, be present at the proximal end of the vessel. The first component may then collect at the distal end of the vessel. The seal may then be inserted into the vessel, for example via the opening thereby defining a first chamber within the vessel that contains the first component. The seal may then engage the one or more proximal projections in the proximal bypass zone. The projection urges a portion of the seal away from the internal wall of the vessel such that one or more channels are opened between the vessel wall and the seal which bypass the seal. The seal may then be moved towards the distal end of the vessel. As this is done, gas that is trapped between the distal end of the vessel and the seal in the first chamber is forced out of the first chamber passed the seal via the one or more channels. The seal then reaches the end of the proximal bypass zone and reengages the internal wall of the vessel at the sealing position. In this position, the first component cannot bypass the seal and is contained in the first chamber.

Thus, by setting the length of the one or more proximal projections and hence the length of the proximal bypass zone according to the volume of first component to be contained, the vessel can be configured such that no air/gas is present in the first chamber once the seal is in the sealing position. A user may wish to exclude air from the first chamber to increase the shelf-life of the first component.

Once the seal is in the sealing position, a second component may be added to the vessel on the opposite side of the seal to the first component. As the seal is in the sealing position, the first component and the second component cannot contact each other. A user can contact the first and second components by engaging the seal with the one or more distal projections in the distal bypass zone. As the seal is moved towards the distal end of the vessel, the first component is forced passed the seal and contacts the second component. The first and second components can then be mixed and may be dispensed from the vessel, for example via an opening at the proximal end of the vessel.

In one embodiment, the one or more proximal projections extend to the proximal end of the vessel. Alternatively or additionally, the one or more distal projections may extend to the distal end of the vessel.

At least a portion of at least one projection may taper towards the proximal end of the vessel. This may be preferred when the seal is configured to be moved from the proximal end of the vessel to the distal end of the vessel.

The invention also provides a method for introducing at least two components into a vessel having a proximal end and a distal end, the method comprising:
(i) introducing a first component into the vessel;
(ii) inserting a seal into the vessel to create a first chamber containing the first component;
(iii) engaging the seal with one or more proximal projections located in a proximal bypass zone of the vessel such that a portion of the seal is urged away from the internal wall thereby opening one or more channels which bypass the seal;
(iv) sliding the seal along the one or more projections towards the first component thereby expelling gas from the first chamber via the one or more channels;
(v) disengaging the seal from the one or more proximal projections thereby closing the one or more channels;
(vi) introducing a second component into the vessel such that the seal separates the second component from the first component.

Steps (ii) and (iii) may occur simultaneously, for example where the one or more proximal projections extend to the proximal end of the vessel.

In one embodiment, the method may further comprise, after step (vi):
engaging the seal with either (a) the one or more proximal projections, or (b) one or more distal projections located in a distal bypass zone of the vessel, thereby opening one or more channels which bypass the seal such that the first component and the second component can contact each other,
wherein the proximal bypass zone and the distal bypass zone are separated by a distance that is greater than or equal to the thickness of the seal.

The method may be performed using any type of vessel described herein.

The seal may have a first position wherein the seal is not engaged with a projection and there is no channel between the first chamber and the second chamber, and a second position wherein the seal is engaged with the one or more projections and one or more channels are present between the first chamber and the second chamber. When the seal is in the first position, there is preferably no liquid communication between the first chamber and the second chamber. The channel(s) are preferably formed between the internal wall of the vessel and the seal, and may allow liquid communication between the first chamber and the second chamber. In some embodiments the channels may allow solids to pass between the chambers. As the seal is capable of defining first and second chambers within the vessel, the vessel, may be referred to as a multi-chambered vessel. It will be appreciated that the relative size of the first and second chambers will change as the seal moves through the vessel.

Such a multi-chambered vessel is useful for keeping two (or more) components separate from one another until a time when the components are to be contacted. This is particularly advantageous where the combination of components is, for example unstable or liable to precipitation or sedimentation over longer periods of time. In the case of food products and beverages for example, the vessel ensures freshness and/or stability of components. Moreover, the vessel allows a user to contact components quickly and safely and ensures error free administration and high dose accuracy because there is no bypass region or similar area in which components can become trapped. The vessel of the invention is configured to allow a user to contact the components at a desired time without having to remove the components from the vessel. This eliminates the possibility of contamination of the components or the user during contacting or mixing of the components.

The seal provides a barrier separating any components contained within the first and second chambers. When a user wishes to establish communication between the first and second chambers, for example to contact the components with one another, the user can actuate the actuator to cause engagement of the seal and the projection(s). The engagement of the seal with the projection(s) urges a portion of the seal away from the internal wall of the vessel. This leads to the formation of one or more channels which link the first chamber to the second chamber. Such channels may be formed in a number of ways. For example, raising of the seal onto the projections may lead to the formation of one or more channels defined between the internal wall, the seal and the projection as contact between the seal and the internal wall is broken by the projection(s). Typically, a channel may form on either side of the projection (or of each projection) as illustrated in the FIG. 4. It will be appreciated that where the vessel comprises multiple projections, a similar interaction may take place between each projection and corresponding portions of the seal. In some embodiments, the one or more projections comprise an opening extending through the entire longitudinal axis of the projection such that the projection forms a tunnel or bridge-like structure. In such embodiments, when the seal engages the projections and is raised onto the projection(s), the opening is exposed and allows communication between the first and second chambers. This may represent the only channel formed between the first chamber and the second chamber upon engagement of the seal with the projection(s). Alternatively, the opening extending through the projection may be complementary to one or more additional channels formed between the internal wall, the seal and the projection(s) as described above.

The vessel is also useful for dispensing multiple components or aliquots/doses of components from the vessel at desired intervals. This is described below with reference to two components, but it will be appreciated that equally, two (or more) doses of the same component could be dispensed using the vessel. It will also be appreciated that a vessel of the invention may comprise more than one seal and corresponding projection(s) as defined herein and therefore more than two components or doses could be dispensed in accordance with the general method described below. In such embodiments, the formation of the channels does not necessarily result in contacting components contained within separate chambers. Instead, prior to engagement of the seal and the projection(s), a first component in a first chamber may be dispensed from the vessel via an outlet, preferably by moving the actuator to a first position. Subsequently, the actuator may be actuated e.g. moved to a second position, causing the seal to engage the projection(s) to open one or more channels as described above, allowing a second component in a second chamber to enter the first chamber. Finally, the second component may be dispensed from the vessel via the outlet, for example by moving the actuator to a third position. The first and third positions may be the same position. For example, the actuator may be a piston and plunging the piston into a chamber of the vessel may facilitate dispensing of components and withdrawing the piston (partially or fully) may facilitate engagement of the seal and the projection(s). Variations on this embodiment for delivering components in different doses/aliquots and/or in different orders will be apparent to the skilled person.

In some embodiments, the vessel is generally cylindrical in shape. In other embodiments, the vessel has a generally rectangular cross section. The vessel may comprise an outlet for dispensing a component, especially a liquid, therefrom. For example, the vessel may be a syringe, preferably a dual-chambered syringe. The syringe may or may not be provided with a needle. The vessel may be a multi-chambered food product or beverage container, for example a bottle or vial. The vessel may comprise any known bottle cap or closure that allows a user to drink from the bottle/vial or to use in anyway suitable for each case the mixture. The vessel may be a cartridge for delivering a cosmetic or a domestic or industrial chemical such as an adhesive or sealant or any of the other components disclosed herein. Any known vessel that is not already provided with a seal defining a first chamber and a second chamber may be provided with a suitable seal in order to practice the present invention.

The seal can be any member capable of separating components stored in different chambers of the vessel. The seal has a surface which may contact the internal wall of the vessel directly or indirectly prior to engagement with the projection(s). The seal or a portion thereof is preferably resiliently deformable such that, as the seal engages the projection(s), at least a portion of the seal deforms so that at least a portion of its internal wall-engaging surface is displaced from the internal wall of the vessel. The deformation of the seal results in the formation of the channel(s). The seal is preferably impermeable to liquids and/or gases. The seal may include a bypass slit that is adapted to open when the seal engages a projection and close when the seal disengages the projection.

In one embodiment, the seal is movable along a longitudinal axis of the vessel and the one or more projections are not movable. For example, the seal may slide within the vessel along the internal wall. In this case, the actuator may cause the seal to move. The actuator may or may not contact the seal directly in order to achieve this. If the actuator does not contact the seal directly, a mechanical linkage may be provided between the actuator and the seal. Alternatively, the actuator may cause the seal to move by exerting pressure on the seal in the manner of a piston. In one embodiment the actuator is in the form of a cap which fits to the vessel and may form a closure at one end of the vessel (for example a screw cap). The cap may comprise a depressible elastic portion. The elastic portion may be configured to increase the pressure within a chamber of the device when depressed to force the seal longitudinally through the vessel to engage the projection(s). Alternatively a mechanical linkage between the elastic portion and the seal may be provided to link the depression of the elastic portion to movement of the seal. The actuator may be incorporated into a lid configured to close an opening in the vessel. The opening may be at a proximal end of the vessel or at a distal end of the vessel. The actuator may comprise a bulb or pump.

In some embodiments, the one or more projections are moveable along a longitudinal axis of the vessel and the seal is not movable. In this case, the actuator will cause the projection(s) to move and may do so directly or indirectly. If the actuator does not contact the projection(s) directly, a mechanical linkage, for example, may be provided between the actuator and the projection(s).

The one or more projections may be an extension of or continuous with the internal wall of the vessel e.g. formed integrally during the manufacturing of the vessel wall. In one embodiment, the projections are provided on the internal wall such that the outer shape of the vessel is not affected or influenced by the projection(s). In other embodiments, the vessel may comprise narrowed or widened portions that accommodate the projection(s). Alternatively, the projection(s) may be discrete structures that are either fixed in position or movably attached to the internal wall after the vessel wall has been formed. The projection(s) may be situated within the first chamber or within the second chamber. The projection(s) are preferably made from a material that is chemically inert so that the projection(s) have no impact on any components contained within the vessel. For example, the projection(s) could be made from the same material as the vessel or the seal. Examples of suitable materials include Polyethylene terephthalate (PET), Polypropylene (PP), Thermoplastic elastomers (TPE), HDPE, LLDPE, LDPE, cyclopoly olefin resin, cyclo olefin copolymer, glass, titanium and aluminium. In choosing the material, one or more of the following factors may be taken into consideration: physicochemical characteristics/properties of the vessel, purpose of the vessel, physicochemical characteristics/properties of the component/s, storage conditions, scope of use and/or way of use etc. Materials and methods may be chosen to minimise friction between the seal and the projection(s) to allow smooth operation.

The optimal number, position, shape and dimensions of the projection(s) depend on various factors. Such factors include but are not limited to the dimensions of the vessel/chambers, the dimensions and deformability of the seal, the number of chambers in the vessel, the force available to cause engagement of the projections and the seal, and the physicochemical properties of any components to be contained within the vessel. In particular, the viscosity of any liquid components may be of relevance. Generally, more viscous liquids may require a larger channel(s) to be formed, and the number, position and dimensions of the projection(s) will be chosen accordingly.

In one embodiment, the one or more projections have a maximum height H extending perpendicularly to a longitudinal axis of the vessel, and the vessel has an internal diameter D, wherein H is less than or equal to about 0.6 D, about 0.5 D, about 0.4 D, about 0.3 D, about 0.2 D, about 0.15 D, about 0.1 D, about 0.05 D, about 0.025 D, about 0.01D, or about 0.005 D. Larger values of H may require the application of a larger force to engage the seal with the projection(s) to the extent necessary to urge the seal away from the internal wall. However, larger values of H may allow for larger channels to be formed. This may be advantageous if, for example, a component that is to pass through the channel has a relatively high viscosity or is a solid such as a powder. The properties of the seal, for example, flexibility, may also influence the dimensions of the projections.

In an embodiment, the one or more projections have a length L extending along a longitudinal axis of the vessel and the seal has a thickness T extending along the longitudinal axis of the vessel, wherein L is substantially equal to or greater than T. This allows the projection to hold a portion of the seal away from the internal wall along the entire thickness of the seal. In this position, the seal and the projection may be referred to as being fully engaged. The length L may exclude any tapered portions of the projection(s). In certain embodiments, this may be necessary to ensure that the channel(s) extend fully between the chambers. The one or more projections may extend to an end wall of the vessel. This allows one or more channels to remain open as the seal is forced towards the end wall. The seal may eventually contact the end wall. Thus, in such embodiments, the seal can be used to force the entire contents of a first chamber into a second chamber. The vessel may comprise blocking means configured to prevent further movement of the seal or projection(s) or both once the seal and the projection(s) are fully engaged. Alternatively, where the actuator is configured to cause either the seal or the projections to move along a longitudinal axis of the vessel the actuator may be configured to prevent further movement of the seal or projection(s) or both once the seal and the projection(s) are fully engaged. In another embodiment, the actuator is configured to cause at least a portion of the seal to disengage the projection and re-engage the internal wall of the vessel after the seal and the projections have become fully engaged, and preferably once any components have been transferred to the desired chamber. This may prevent backflow of one or both of the components.

The vessel may comprise blocking means within the vessel to prevent the seal moving towards the actuator. For example, if the actuator is a plunger, withdrawing the plunger partially from the vessel may cause the seal to move towards the plunger by suction. Similarly, if the actuator comprises an elastic cap on a bottle or vial, release of the cap may cause the seal to move towards the cap due to suction. Blocking means may be provided to limit or prevent such movement. Such blocking means may take the form of one or more additional projections extending into the vessel over which the seal is not able to pass.

The vessel may comprise two or more, three or more, four or more, five or more, six or more, seven or more, eight or more, nine or more, ten or more, eleven or more, or twelve or more projections. More projections may be preferred if a component contained or to be contained within the chamber is highly viscous or a solid. The projection(s) may have a proximal end and a distal end. The proximal end may come into contact with the seal before the distal end. If more than one projection is used, the proximal end of all of the projections may be aligned, allowing all projections to engage the seal simultaneously. Alternatively, the proximal end of the projections may be staggered so that the projections do not all engage the seal simultaneously. This may provide for smoother operation. The projections may be (i) evenly spaced in a ring around the internal wall of the vessel, or (ii) arranged around the internal wall of the vessel in groups of, for example, two, three, four, five or six. In one embodiment, each projection within a group is separated by a distance d1 and each group is separated by a distance d2, wherein d1 is less than d2. In another embodiment, the projection may extend circumferentially around a portion of the inner wall of the vessel. For example, the projection may extend around at least about 5%, about 10%, about 20%, about 30%, about 40%, about 50%, about 60%, about 70%, about 80%, about 90%, about 95%, about 99% of the circumference of the inner wall of the vessel (or of the equivalent parameter if the vessel is not cylindrical). The projection may not extend around the entire circumference of the inner wall. In this case, a gap is left between the two ends of the projection and this may form a channel between the first and second chamber once the seal and the projection are engaged.

Two or more projections of this type may be aligned giving rise to a "split ring" appearance.

The one or more projections may be generally rectangular, triangular, circular or trapezoidal in cross section. The one or more projections may be tapered. Preferably the projection tapers towards the seal when the seal is in its starting position i.e. pre-engagement with the projection. In one embodiment, the projection(s) have a proximal end and a distal end, wherein the proximal end is the first portion of the projection to engage the seal during operation. The proximal end and/or the distal end may be tapered. For example, the vessel may be configured such that the seal can engage the projection(s) from both a proximal and a distal direction, in which case it is preferred if both proximal and distal ends of the projection(s) are tapered. A tapered portion allows for smoother engagement of the seal with the projection(s) by providing a ramp for the seal and hence the force necessary to urge the seal away from the internal wall of the vessel may be reduced. The taper may be in the form of continuous slope or one or more steps. The slope may have a constant gradient or a variable gradient. The one or more projections may include a barbed or hooked region towards a distal end of the projection, adapted to cause partial deformation of the seal as the seal passes over the barb or hook. This may improve fluid flow passed the seal and the air/gas exclusion process described herein.

The actuator may comprise a piston. If the actuator comprises a piston, the piston may be at least partially received within the first or second chamber of the vessel. A piston may be a preferred if the chamber contains a fluid i.e. a liquid or a gas or a combination of liquid and gas. The piston may be configured to cause engagement of the projection(s) and seal when it is plunged into a chamber thereby increasing pressure within the chamber and "pushing" the seal towards the projection(s), and/or when it is withdrawn from a chamber, thereby reducing the pressure within a chamber and "pulling" the seal towards a projection. Alternatively, the actuator, which may be a piston, may be directly or indirectly coupled to the seal and/or projection (s) so that engagement of the seal and the projection(s) does not rely on changes in pressure. The starting position of the seal relative to the projection(s) may determine which action (plunging or withdrawing) is required in order to cause the seal and the projection(s) to engage one another.

In an embodiment, the piston is located within the second chamber, the projection(s) are located within the first chamber and the piston is configured to cause the seal to move longitudinally through the second chamber to engage the projection(s).

The vessel may contain or be suitable for containing a solid component and/or a liquid component in one or more of its chambers. In one embodiment, the first chamber contains or is suitable for containing a first component and the second chamber contains or is suitable for containing a second component. The first component may be a liquid component or a solid component. The second component may be a liquid or a solid component. In an embodiment, the first chamber contains or is suitable for containing a solid component and the second chamber contains or is suitable for containing a liquid component. In another embodiment, both the first and second chambers contain or are suitable for containing liquid components. In another embodiment, both the first and second chambers contain or are suitable for containing solid components. The terms "solid" and "liquid" should be considered to include, for example, gels, foams and powders. The term "solid" includes semi-solid substances. The term "contains" does not necessarily exclude the presence of other substances within each chamber. For example, a chamber containing a solid component, may also contain gas and/or a liquid. A chamber containing a liquid component may also contain a solid and/or a gas. Contacting or mixing of the first component and the second component may lead to the formation of, for example, a suspension, a dispersion, a solution, an emulsion or a mixture. A liquid component may or may not be a solvent or diluent suitable for reconstituting or dissolving a solid component.

One or both of the first and second components may comprise a pharmaceutical agent or may be a pharmaceutical formulation. Alternatively, one or both of the first and second components may be a non-pharmaceutical formulation. A pharmaceutical formulation or a non-pharmaceutical formulation may be formed once the components have been contacted.

Pharmaceutical formulations/agents may contain any active pharmaceutical ingredient or a combination of ingredients and may be in any form. For example, a pharmaceutical formulation may be lyophilised, non-lyophilised, microencapsulated, nanoencapsulated, freeze dried, and/or may be provided as a tablet, gel, capsule, powder, paste, cream, ointment or solution.

Pharmaceutical formulations/agents may be characterised as, for example, biopharmaceuticals, biologicals, biomaterials, vaccines, peptides, small molecules, antibodies, hormones, corticosteroids, anti-inflammatories, antihistamines, antibiotics, anticoagulants, glycosaminoglycans, polysaccharides etc.

Non pharmaceutical formulations/agents may contain any ingredient or a combination of ingredients and may be lyophilised, non-lyophilised, microencapsulated, nanoencapsulated, freeze dried, and/or may be provided as a tablet, gel, capsule, powder, paste, cream, ointment, or solution.

Non pharmaceutical formulations/agents may be characterised as, for example, nutrition and/or health products, food products, beverages, food supplements, cosmetics or any other industrial or domestic chemical e.g. adhesives, sealants, glues, fertilisers, pesticides, fungicides, herbicides, miticides. Food products, beverages and supplements may comprise or consist essentially of one or more sugars such as glucose or dextrose, a stimulant such as caffeine or taurine, one or more proteins such as whey protein, carbohydrates, complex carbohydrates, resistant carbohydrates, monosaccharide, oligosaccharides, polysaccharides, one or more vitamins, minerals, micronutrients, an iron supplement or combinations thereof. Examples include energy tablets, protein supplements, vitamin supplements, PUFAs, LCPUFAs, MUFAs, SCPUFA, essential oils, flavouring agents, sweetening agents.

Any of the chambers may be treated to minimise or exclude air/oxygen once a component or components have been introduced into the chamber, for example by flushing the chambers with nitrogen or carbon dioxide. Alternatively, or additionally, air/oxygen may be removed from or reduced within a chamber by using a seal in combination with one or more projections. This can be achieved using the principle described herein that engagement of a seal with a projection causes one or more channels to open between the internal wall of the vessel and the seal. By engaging the seal with a projection and moving the seal towards an end wall of the vessel, any air/oxygen trapped between the seal and the end wall is forced passed the seal via the channels.

The length of a projection can be used to control how much air/oxygen is removed from the chamber. Longer projections mean that the seal can advance further into the vessel whilst maintaining a channel between the internal wall and the seal through which the air/oxygen can escape.

Thus, more air/oxygen can be removed from a chamber of the vessel by using a projection which extends further along the longitudinal axis of the vessel. Preferably, the projection terminates leaving enough space between the projection and any component stored within the chamber for the seal to re-engage the internal wall and hence prevent the component from escaping past the seal. Thus, by moving the seal towards the component, air/oxygen can be reduced or removed from a chamber in which the component is stored.

When a user wishes to transfer the component to the next chamber, the seal is engaged with a projection. This may be the projection used to remove air from the chamber ("first projection") or may be a separate projection ("second projection") spaced longitudinally from the first projection. In the latter embodiment, the first projection and the second projection are preferably separated by a gap i.e. a portion of the internal wall of the vessel where no projection is present. The length of the gap is preferably greater than or equal to the thickness of the seal. This allows the seal to re-engage the internal wall of the vessel once sufficient air has been removed from the chamber, but before the component is forced past the seal via the channels.

The first component or a portion thereof and/or the second component or a portion thereof can move through the channel(s) formed by engagement of the seal and the projection(s). In certain embodiments, this allows the first and second components to contact one another. In one embodiment, the vessel is configured to permit movement in a single direction through the channel(s). For example, a pressure gradient may ensure that components can move through the channel(s) in only a single direction. A pressure gradient may be created by a user actuating the actuator, for example if the actuator is a piston. In some embodiments, the physical properties of the components may prevent one of the components moving through the channel(s). For example, where a first component is a liquid and a second component is a solid, the liquid may be able to pass through the channel(s) whereas the solid may be confined to its starting chamber due to its size or conformation. However, in some embodiments, the solid component is capable of moving through the channel(s). This may be the case if the solid component is in the form of, for example, a gel or a powder. In some embodiments, the entire second component is able to move into the first chamber via the channel(s). In other embodiments, the entire first component is able to move into the second chamber via the channel(s).

The vessel may comprise more than two chambers. In such embodiments, further seals may be provided to define additional chambers. For example, three chambers can be defined using two seals, four chambers can be defined using three seals, five chambers can be defined using four seals etc. Such vessels may be provided with longitudinally spaced sets of one or more projections each set being configured to engage a seal in the manner described herein. For example, each chamber may comprise a bypass zone comprising one or more projections. The actuator may be configured to cause engagement of each seal and its corresponding projection(s). Preferably, engagement between each seal and its projection(s) does not occur simultaneously. This allows a user to control movement of components through chambers in a sequential manner. For example, it may be desirable to contact a first component initially contained in a first chamber with a second component initially contained in a second chamber for a period of time before contacting that mixture of first and second components with a third component contained within a third chamber. This can be achieved by first causing a first seal separating the first and second chambers to engage its corresponding projection(s) and subsequently causing a second seal separating the second and third chambers to engage its corresponding projection(s).

The invention also provides a kit comprising (i) an accessory for a vessel, the accessory comprising one or more projections as defined herein, and (ii) securing means for securing the accessory to an internal wall of the vessel.

The vessel may be any vessel described herein. The vessel may be a vessel having a single chamber. The kit may further comprise any type of vessel described herein. The kit may further comprise one or more components as described herein. Such components may be contained within the vessel or provided separately.

In one embodiment, the kit further comprises a seal suitable for defining separate chambers in a vessel. The kit may be used to convert a single chambered vessel into a dual-chambered vessel suitable for containing a first component separately from a second component and, for example, contacting the components at a desired time or dispensing the components from the vessel at desired intervals. If the starting vessel has more than one chamber already, such a kit can be used to add an additional chamber to the vessel. Communication between the new chamber and one of the exiting chambers can be controlled using the interaction between the seal and the projections as described herein.

The securing means may be of any type capable of securing the accessory to the internal wall. The projection(s) may or may not contact the internal wall directly once secured in position. Once secured, the projection(s) may be immovable, for example if the seal is movable along a longitudinal axis of the vessel, or the projection(s) may be movable along a longitudinal axis of the vessel, for example if the seal is immovable.

In one embodiment, the securing means are an adhesive. The projection(s) may be fixed directly or indirectly to the internal with an adhesive. In another embodiment, the securing means may comprise a support structure to which the projection(s) are fixed. The support structure may comprise a vessel wall-engaging portion which engages at least one wall of the vessel and holds the projection(s) in the appropriate position. The vessel wall may comprise a slot or groove into which at least a portion of the support structure can be inserted. For example two or more projections may be fixed to an annular member configured to engage a corresponding groove running around an internal circumference of the vessel. In other embodiments, a groove in the vessel wall may not be required. Instead, the support structure may be configured to engage an internal end wall of the vessel or blocking means within the vessel which prevent the support structure from moving once inserted into the vessel. In such embodiments, the support structure may take the form of a "tunnel". The projection(s) may be provided within the tunnel and may protrude from the tunnel. In such an embodiment, the projections may, upon engagement with the seal, cause the seal to deform such that it can at least partially enter the tunnel. As the projection(s) are provided within the tunnel, once the seal and the projection(s) are fully engaged, a portion of the seal will be held away from the internal wall of the tunnel such that one or more channels may form between the seal and the internal wall of the tunnel. The thickness of the tunnel may be small relative to the diameter of the vessel. For example, a leaf of aluminium may be used. The securing means may include a hooked portion that is adapted engage a rim of an opening in the vessel.

The securing means may comprise an insert sleeve adapted fit inside the vessel, wherein the one or more projections are secured to an interior wall of the sleeve. The insert sleeve is preferably a tight fit within the vessel. The seal may be configured to fit inside sleeve. For example, the seal may have a diameter that is substantially equal to an internal diameter of the sleeve.

The accessory may be comprise one or more proximal projections defining a proximal bypass zone when the accessory is fitted inside a vessel, and one or more distal projections defining a distal bypass zone when the accessory is fitted inside a vessel. The proximal and distal bypass zones may be separated by a distance that is greater than or equal to the thickness of the seal of the kit.

The invention also provides a method of converting a vessel having a first chamber into a vessel having a first chamber and a second chamber, the converted vessel being capable of controlling communication between the first chamber and the second chamber, the method comprising
 (i) inserting a seal into a vessel having a first chamber to define within the vessel a first chamber and a second chamber; and
 (ii) securing an accessory as defined herein to an internal wall of the vessel at a position where the one or more projections can engage the seal upon movement of the seal or the one or more projections along a longitudinal axis of the vessel.

In one embodiment, the accessory may be secured to the vessel before the seal is inserted. This may be preferred if the securing means is provided in the form of an insert sleeve as described above.

The securing step may be performed using any securing means described herein. A shrink-fitting technique may be used to secure the accessory to the vessel. This involves heating or cooling the accessory and/or the securing means or the vessel before assembly and allowing the components to return to ambient temperature after assembly. The relative expansion or contraction of one component relative to another component results in a tight fit after assembly.

The method may further comprise loading a first component into the first chamber and a second component into the second chamber. Any first and second components described herein may be used. The vessel may comprise an actuator as described herein. The vessel may be any vessel described herein. The method may include reducing the levels of or excluding air/oxygen from one or more of the chambers using any of the methods described herein.

The invention also provides a method of contacting a first component and a second component wherein the first component is contained within a first chamber of a multi-chambered vessel and the second component is contained in a second chamber of the vessel, wherein the first component and the second component are separated by a seal, the method comprising
  (i) providing one or more projections on an internal wall of the vessel
  (ii) engaging the seal with the one or more projections to urge a portion of the seal away from the internal wall thereby opening a channel between the first chamber and the second chamber such that the first component and the second component can contact one another.

The vessel, projection(s) and components may be as described herein. Preferably the seal is engaged with the projection by actuating an actuator as described herein.

The invention also provides a method of dispensing multiple components or multiple doses of one or more components from a multi-chambered vessel wherein a first component or first dose is contained within a first chamber of a multi-chambered vessel and a second component or a second dose is contained in a second chamber of the vessel, the first component or first dose being separated from the second component or second dose by a seal, the method comprising:
  (i) providing one or more projections on an internal wall of the vessel
  (ii) dispensing the first component or first dose from the vessel via an outlet
  (iii) engaging the seal with the one or more projections to urge a portion of the seal away from the internal wall thereby opening a channel between the first chamber and the second chamber and allowing the second component or second dose to enter the first chamber via the channel
  (iv) dispensing the second component or second dose from the vessel via an outlet.

The vessel, projection(s) and components may be as described herein. Preferably the seal is engaged with the projection by actuating an actuator as described herein. Dispensing of the components or doses via the outlet may or may not be linked to actuation of the actuator. For example, if the actuator is a piston, plunging of the piston into a chamber of the device may force a component out of the device via an outlet. Alternatively, a component or dose thereof may be dispensed simply by tipping or pouring the component out of the device via the outlet. This may be appropriate, if for example the vessel is a bottle, wherein the outlet is the opening of the bottle. The outlet from which the first component is dispensed may or may not be the same outlet from which the second component is dispensed. The method of contacting a first component and a second component described herein may be combined with one or more steps of the method of dispensing multiple components or multiple doses of one or more components from a multi-chambered vessel described herein. In this way, a first component and a second component (for example) may be contacted with one another, and subsequently one or more doses of the combined components may be dispensed from the vessel. This may be preceded or followed by the dispensing of a different component or combination of components (which may be contained in a separate chamber) from the vessel.

The projections of the present invention reduce the internal cross section of the vessel thereby preventing the seal from creating a tight seal inside the vessel. This allows fluid to bypass the seal when the seal engages a projection. A similar effect can be achieved by incorporating one or more bypass channels into an internal wall of the vessel to create a bypass zone having a cross section that is greater than the cross section of the seal. Thus, when the seal is located in such a bypass zone, fluid e.g. liquid or gas or flowable solid, can flow passed the seal via the bypass channel.

Thus, the invention also provides a vessel having a proximal end and a distal end and comprising
  a removable seal for defining first and second chambers within the vessel,
  an actuator configured to move the seal through the vessel, and
  a bypass zone comprising one or more bypass channels in an internal wall of the vessel, wherein the bypass zone has a cross section that is greater than the cross section of the seal such that the seal cannot prevent communication between the first and second chambers when it is positioned in the bypass zone.

Also provided is a vessel having a proximal end and a distal end and comprising
  a removable seal for defining first and second chambers within the vessel,
  a proximal bypass zone comprising one or more proximal bypass channels in an internal wall of the vessel,
  a distal bypass zone comprising one or more distal bypass channels on in internal wall of the vessel, and
  an actuator configured to move the seal through the vessel,
  wherein the proximal and distal bypass channels each have a cross section that is greater than the cross section of the seal, such that the seal cannot prevent communication between the first and second chambers when it is positioned in the proximal bypass zone or in the distal bypass zone, and
  wherein the proximal bypass zone and the distal bypass zone are separated by a distance that is greater than or equal to the thickness of the seal.

A bypass channel may be provided by creating a thinner portion of the internal wall of the vessel. In this embodiment, the outer wall of the vessel will not be bulged. Alternatively, a bypass channel may be created by widening a portion of the vessel such that a bulge in the outer wall is present. The vessel may include multiple bypass zones, each comprising one or more bypass channels. The bypass zones may be separated by sealing zones which have a cross section that is substantially equal to the cross section of the seal. Bypass zones may be separated by a distance that is greater than or equal to the thickness of the seal. Bypass channels within each bypass zone may be spaced apart in the manner described above in relation to spacing of the projections. For example, a bypass zone may comprise two circumferentially spaced bypass channels.

The invention also provides a method for introducing at least two components into a vessel having a proximal end and a distal end, the method comprising:
(i) introducing a first component into the vessel;
(ii) inserting a seal into the vessel to create a first chamber containing the first component;
(iii) moving the seal to a proximal bypass zone of the vessel which comprises one or more proximal bypass channels, the proximal bypass zone having a cross section that is greater than the cross section of the seal;
(iv) moving the seal through the proximal bypass zone towards the first component thereby expelling gas from the first chamber of the vessel via the one or more proximal bypass channels;
(v) moving the seal out of the proximal bypass zone to a sealing position;
(vi) introducing a second component into the vessel such that the seal separates the second component from the first component.

Steps (ii) and (iii) may occur simultaneously.

After step (vi), the method may also include moving the seal (a) back into the proximal bypass zone, or (b) into a distal bypass zone of the vessel thereby allowing the first component and the second component to contact each other. In this embodiment, the distal bypass zone comprises a distal bypass channel and has a cross section that is greater than the cross section of the seal, and the proximal bypass zone and the distal bypass zone are separated by a distance that is greater than or equal to the thickness of the seal.

The invention also provides a kit comprising an insert sleeve for a vessel and a seal, wherein the insert sleeve is adapted to fit inside the vessel and comprises one or more sealing zones having a cross section substantially equal in size to the cross section of the seal and one or more bypass zones having a cross section greater than the cross section of the seal. The insert sleeve may be secured to the vessel using any of the securing means or methods disclosed herein.

Such a kit provides a convenient means to add bypass zones to a standard vessel.

The number and position of bypass channels can be varied according to a user's requirements as described above with reference to the embodiments that include one or more projections. For example, the insert sleeve may include a proximal bypass zone including a proximal bypass channel and a distal bypass zone including a distal bypass channel. The proximal and distal bypass zones may be separated by a distance that is greater than or equal to the thickness of a seal that is to be used with the kit. Each bypass zone may include multiple bypass channels.

Any type of vessel, actuator or first and second components described herein with reference to the embodiments which include projections can also be used with the bypass channel embodiments. Vessels of the invention may be provided with a combination of bypass channels and projections if desired.

Vessels provided with one or more bypass channels may be used for any of the methods described above with reference to embodiments which include one or more projections mutatis mutandis, including but not limited to methods for dispensing multiple components or aliquots/doses of components from a vessel at desired intervals.

Further aspects of the invention are described in the following numbered clauses:
1. A multi-chambered vessel comprising a first chamber, a second chamber and a seal separating the first and second chambers, the vessel further comprising one or more projections on an internal wall thereof, and an actuator configured to cause the seal and the one or more projections to engage one another, wherein the one or more projections are configured to urge a portion of the seal away from the internal wall upon engagement with the seal to open one or more channels between the first chamber and the second chamber.
2. The multi-chambered vessel of clause 1, comprising a first component contained within the first chamber and a second component contained within the second chamber.
3. The multi-chambered vessel of clause 2, wherein the first component is a solid component and the second component is a liquid component.
4. The multi-chambered vessel of clause 3, wherein the solid component is a pharmaceutical formulation comprising an active pharmaceutical agent and the liquid component is a diluent.
5. The multi-chambered vessel of clauses 1-4, wherein the seal is movable along a longitudinal axis of the vessel and the one or more projections are not movable.
6. The multi-chambered vessel of any one of clauses 1-4, wherein the one or more projections are moveable along a longitudinal axis of the vessel and the seal is not movable.
7. The multi-chambered vessel of clauses 1-6, wherein the actuator comprises a piston.
8. The multi-chambered vessel of clauses 1-7, wherein the one or more projections are situated within the first chamber.
9. The multi-chambered vessel of clauses 1-8, wherein the one or more projections are generally rectangular, triangular, circular or trapezoidal in cross section.
10. The multi-chambered vessel of clauses 1-9, wherein the one or more projections taper towards the seal.
11. The multi-chambered vessel of clauses 1-10, wherein the one or more projections have a length L extending along a longitudinal axis of the vessel and the seal has a thickness T extending along the longitudinal axis of the vessel, wherein L is substantially equal to or greater than T.
12. The multi-chambered vessel of any clauses 1-11, wherein the one or more projections have a maximum height H extending perpendicularly to a longitudinal axis of the vessel, and the vessel has an internal diameter D, wherein H is less than or equal to 0.1 D.
13. The multi-chambered vessel of clauses 1-12, wherein the vessel comprises two, three, four, five, six, seven, eight, nine, ten, eleven, or twelve projections.
14. The multi-chambered vessel of clause 13, wherein the projections are (i) evenly spaced in a ring around the internal wall of the vessel, or (ii) arranged around the internal wall of the vessel in groups of two, three, four, five or six, wherein each projection within a group is separated by a distance d1 and each group is separated by a distance d2, wherein d1 is less than d2.
15. The multi-chambered vessel of any one of clauses 1 to 12, wherein the vessel comprises a projection which extends circumferentially around a portion of the inner wall of the vessel.
16. The multi-chambered vessel of any of clauses 1-15, wherein the one or more projections comprises an opening extending through an entire longitudinal axis of the projection.

17. The multi-chambered vessel of clause 16, wherein the opening extending through the projection is the channel between the first chamber and the second chamber or one of the channels extending between the first chamber and the second chamber.
18. The multi-chambered vessel of any of clauses 1-17, wherein the vessel is a syringe.
19. A kit comprising (i) an accessory for a vessel, the accessory comprising one or more projections as defined in any one of the preceding claims, and (ii) securing means for securing the accessory to an internal wall of a vessel.
20. The kit of clause 19, further comprising a seal suitable for defining separate chambers in a vessel.
21. A method of converting a vessel having a first chamber into a vessel having a first chamber and a second chamber, the converted vessel being capable of controlling communication between the first chamber and the second chamber, the method comprising
   (i) inserting a seal into a vessel having a first chamber to define within the vessel a first chamber and a second chamber; and
   (ii) securing an accessory as defined in claim 17 to an internal wall of the vessel at a position where the one or more projections can engage the seal upon movement of the seal or the one or more projections along a longitudinal axis of the vessel.
22. A method of contacting a first component contained within a first chamber of a multi-chambered vessel with a second component contained within a second chamber of the vessel and separated from the first component by a seal, the method comprising
   (i) providing one or more projections on an internal wall of the vessel
   (ii) engaging the seal with the one or more projections to urge a portion of the seal away from the internal wall thereby opening a channel between the first chamber and the second chamber such that the first component and the second component can contact one another.
23. A method of dispensing multiple components or multiple doses of one or more components from a multi-chambered vessel wherein a first component or first dose is contained within a first chamber of a multi-chambered vessel and a second component or a second dose is contained in a second chamber of the vessel, the first component or first dose being separated from the second component or second dose by a seal, the method comprising:
   (i) providing one or more projections on an internal wall of the vessel
   (ii) dispensing the first component or first dose from the vessel via an outlet
   (iii) engaging the seal with the one or more projections to urge a portion of the seal away from the internal wall thereby opening a channel between the first chamber and the second chamber and allowing the second component or second dose to enter the first chamber via the channel
   (iv) dispensing the second component or second dose from the vessel via an outlet.

Preferred features of each aspect of the invention are as for each of the other aspects *mutatis mutandis*.

BRIEF DESCRIPTION OF THE DRAWINGS

FIGS. 9A-9E: schematic illustration showing how gas can be removed from a chamber of a vessel.

FIGS. 15A and 15B: a cross section of an insert sleeve for a vessel having a sealing zone and a bypass zone (A) and a vessel to which the insert sleeve has been fitted (B).

DESCRIPTION OF THE FIGURES

Figure 1A:
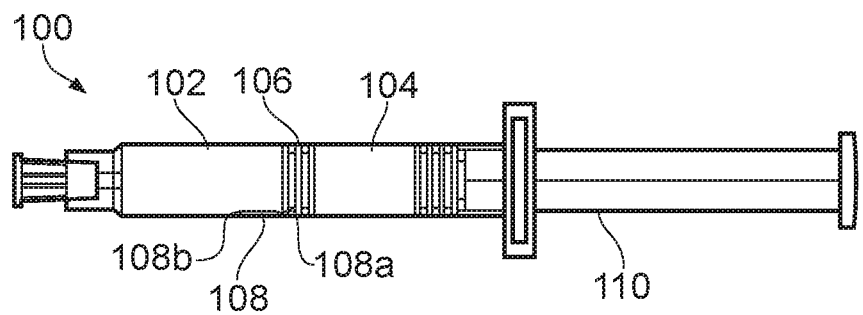
FIGS. 1A-1C: plan, side and cross section views of an embodiment of a multi-chambered vessel according to the invention.
Figure 1B:
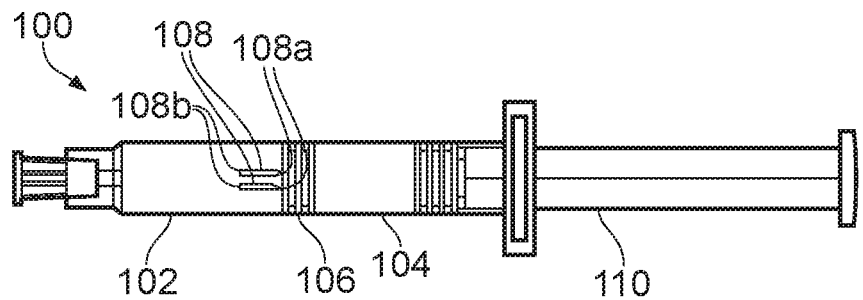
Figure 1C:
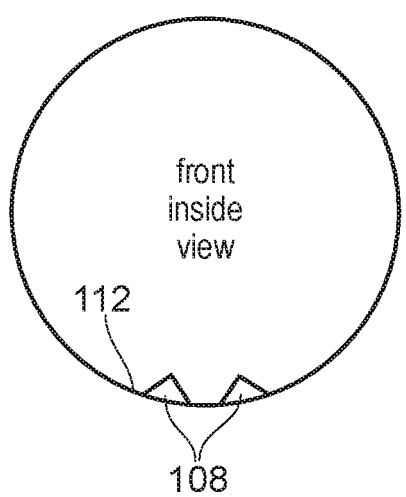
Figure 10:
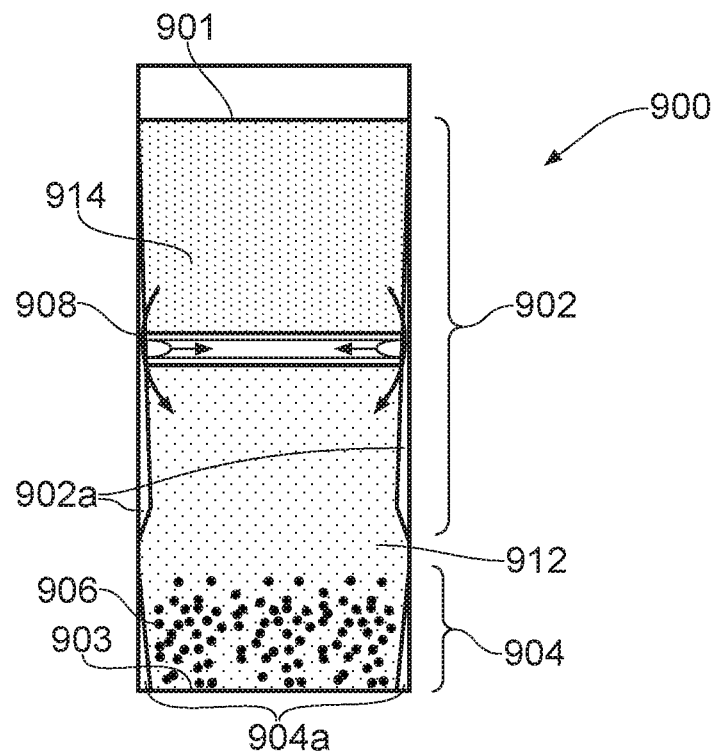
FIG. 10: schematic diagram showing an alternative to step E of FIG. 9.

FIG. 1A shows a side view of a multi-chambered vessel 100, specifically a syringe, comprising a first chamber 102, a second chamber 104 and a seal 106 separating the first and second chambers. Provided on an internal wall of the first chamber 102 are two projections 108. The projections have a proximal end 108*a* and a distal end 108*b*. The proximal ends 108*a* are aligned such that they can engage the seal 106 simultaneously. The vessel 100 further comprises an actuator in the form of a plunger 110 configured to cause engagement of the seal 106 with the projections 108. FIG. 1B shows a plan view of the syringe shown in FIG. 1B. FIG. 10 shows a cross section along the longitudinal axis of the vessel of FIGS. 1A and 1B. The two projections 108 are positioned on an internal wall 112 of the vessel.

Figure 2A:
FIGS. 2A and 2B: plan and side views of a projection according to the invention.
Figure 2B:

FIGS. 2A and 2B show an embodiment of projections of the invention. In this embodiment, the projection is tapered as can be seen in FIG. 2B.

Figure 3:
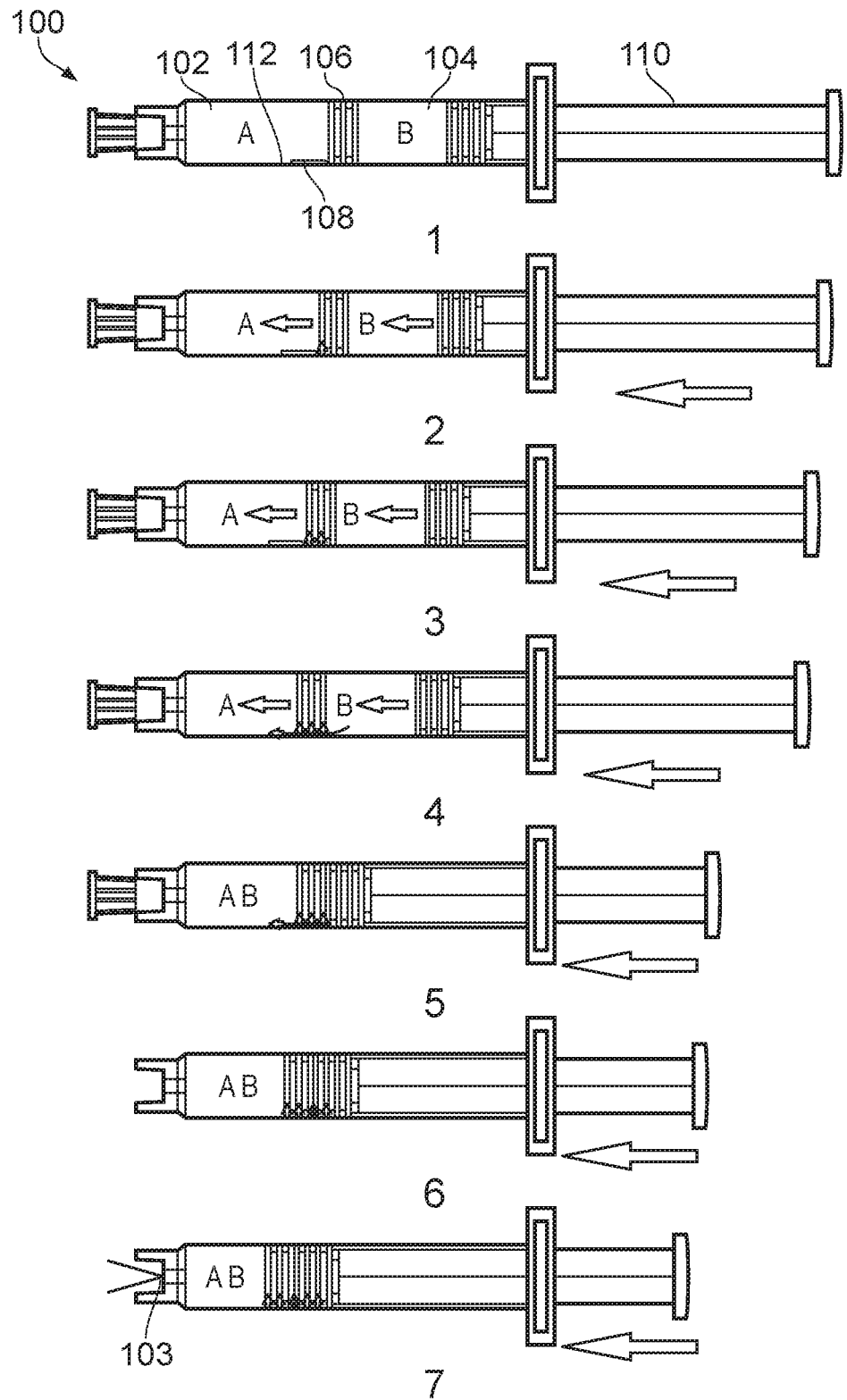
FIG. 3: schematic diagram showing the operation of a multi-chambered vessel according to an embodiment of the invention (side view).

The engagement of the seal and the projections to cause the formation of channels will be described with reference to FIG. 3. The first chamber 102 contains first component A and the second chamber 104 contains a second component B. In this embodiment B is a liquid. The plunger 110 is actuated forcing the seal 106 to move along a longitudinal axis of vessel 100 to engage the projections 108 as shown in step 2. The projections 108 urge a portion of seal 106 away from the internal wall of the vessel 100. Step 4 shows the seal 106 and the projections 108 in a fully engaged position where the projections 108 hold a portion of the seal 106 away from the internal wall 112 along the entire thickness T of the seal 106 to form channels connecting the first chamber 102 and the second chamber 104. Component B can then move through the channels into the first chamber 102 and contact component A. In this embodiment, the thickness T of the seal 106 is substantially equal to the length L of the projections 108. At step 5, all of component B has been forced into the first chamber 102. In step 6, a portion of the seal 106 has disengaged the projections 108 and re-engaged the internal wall 112 and, as the plunger 110 pushes the seal 106 further over the projections 108, more of the seal 106 may disengage the projections and re-engage the internal wall 112. The mixture of components A and B is then expelled through an outlet 103 in the vessel (step 7).

Figure 4:
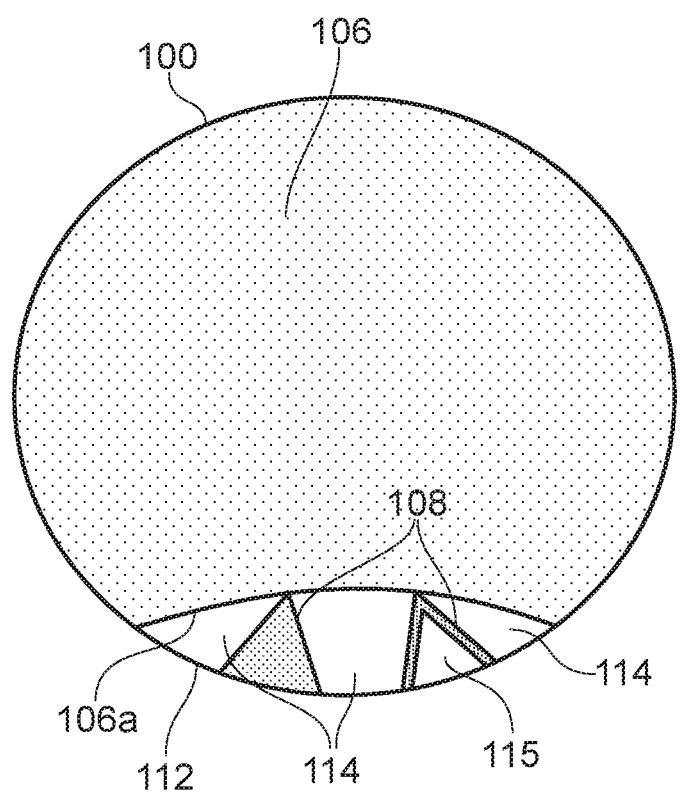
FIG. 4: cross section of a multi-chambered vessel according to the invention showing channels formed by the engagement of projections with a seal.

FIG. 4 shows a cross section of a vessel 100 according to an embodiment of the invention. The seal 106 and the projections 108 are in the fully engaged position. A portion 106a of the seal 106 is held away from the internal wall 112 of the vessel 100 meaning that channels 114 are formed between the internal wall 112 and the seal 106. The channels 114 facilitate communication between the first chamber and the second chamber. In this embodiment, the projection(s) 108 have a triangular cross section. One of the projection(s) 108 comprises an opening 115 extending through the entire longitudinal axis of the projection 108 to form a tunnel which represents an additional channel 114 through which one or more components may pass.

Figure 5A:
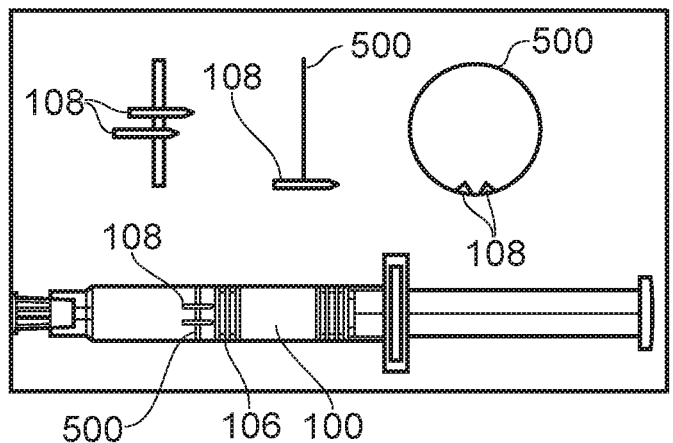
FIGS. 5A-5C: three embodiments of projections fixed to securing means.

FIG. 5A shows plan, side and cross section views of projections 108 fixed to securing means 500. Also shown is a vessel to the projections 108 have been fitted. In this embodiment, the securing means 500 is in the form of an annular member configured to engage a corresponding groove running around an internal circumference of a vessel 100. The projections 108 provided in a staggered formation and are tapered towards the seal 106.

Figure 5B:
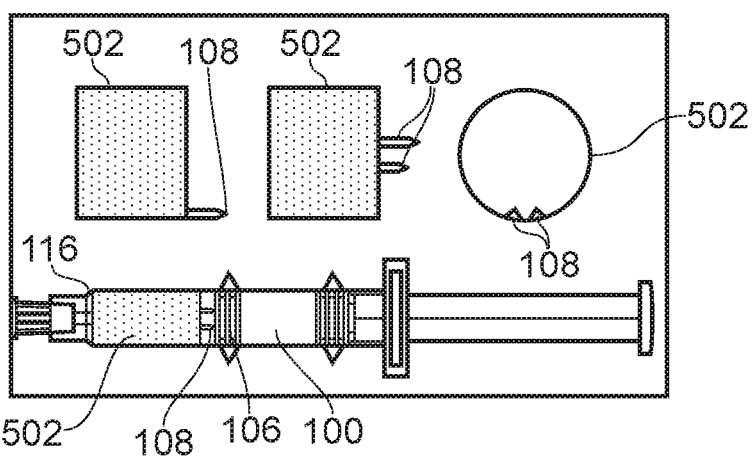

FIG. 5B shows plan, side and cross section views of projections 108 fixed to securing means 502. Also shown is a vessel to the projections 108 have been fitted. In this embodiment, the securing means 502 is in the form of a tunnel. The tunnel fits within the body of the vessel and abuts an end wall 116 of the vessel 100, which keeps the securing means 502 and projections 108 in the correct position inside the vessel. The projection(s) 108 protrude from the tunnel. When a seal 106 engages the projections 108, the seal 106 partially deforms and at least a portion of the seal 106 may enter the tunnel.

Figure 5C:
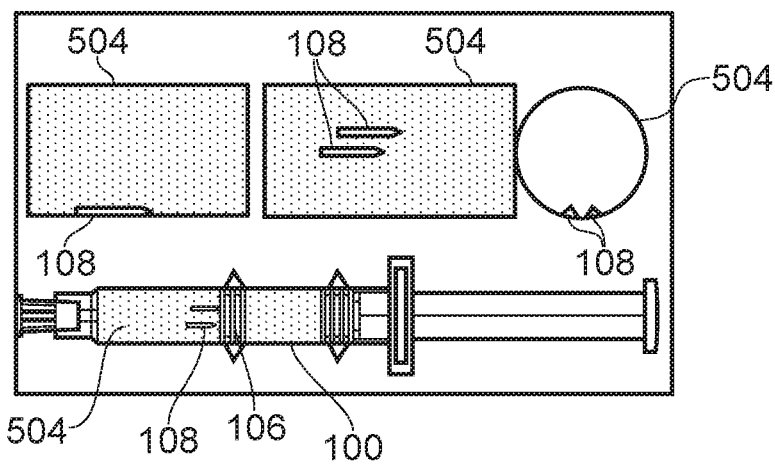

FIG. 5C shows plan, side and cross section views projections 108 fixed to securing means 504. In this embodiment, the securing means 504 is in the form of a tunnel. Also shown is a vessel to which the projections 108 have been fitted. The tunnel extends through the entire interior of the vessel 100. A seal 106 is provided within the tunnel and forms a seal against the internal wall of the tunnel rather than against the wall of the vessel 100 itself. In this embodiment, the two projections 108 are fixed to an internal wall of the securing means 504. Upon engagement of the seal 106 with the projections 108, the seal partially deforms and channels are formed between the internal wall of the securing means 504 and the seal 106.

Figure 6:
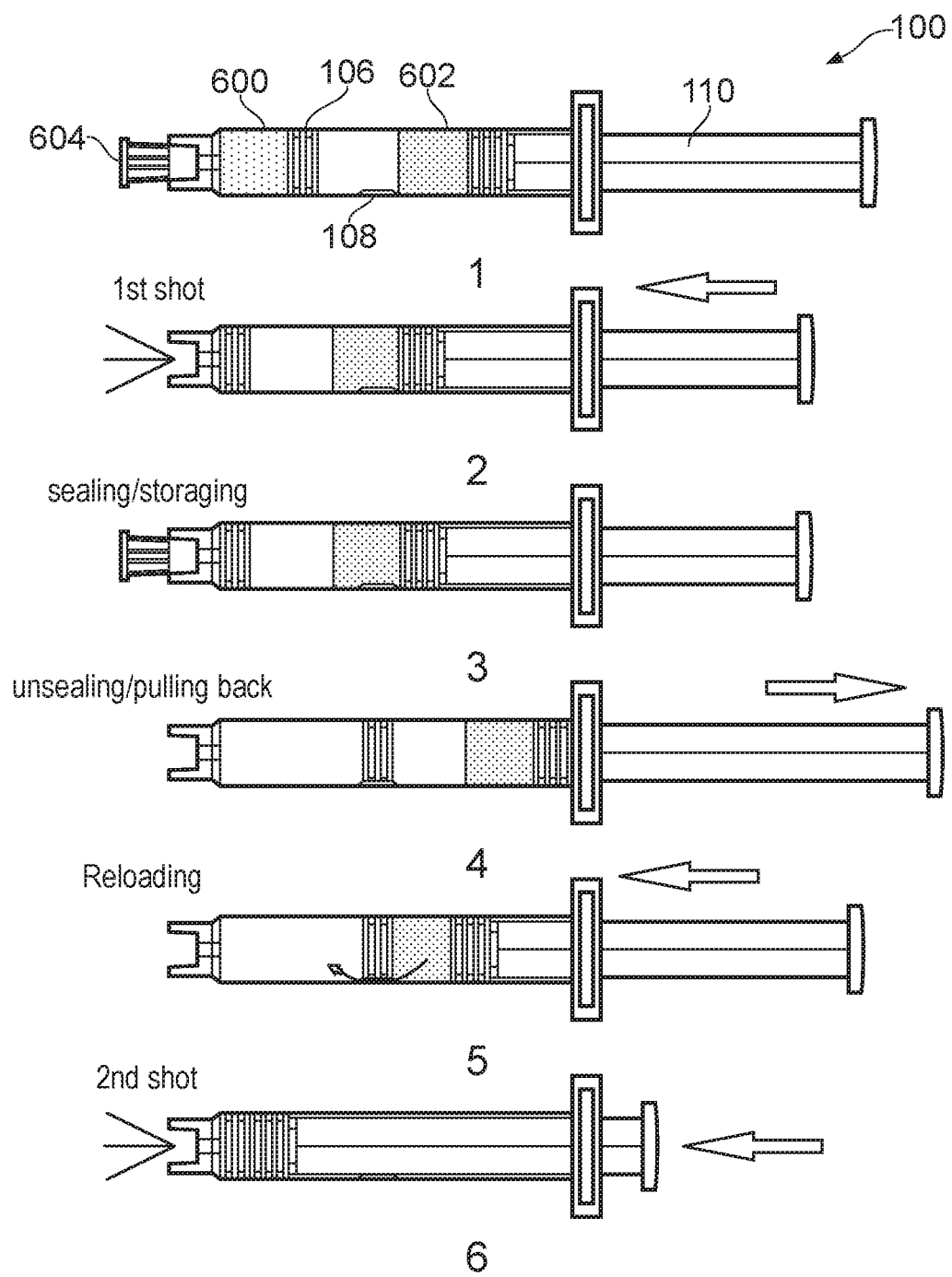
FIG. 6: schematic illustration of a method of dispensing multiple components from a multi-chambered vessel.

FIG. 6 is a schematic illustration of a method of dispensing multiple components from a multi-chambered vessel. In step 1, a first component 600 is provided in a first chamber of the vessel 100 and a second component 602 is provided in a second chamber of the vessel 100. A seal 106 separates the first component 600 from the second component 602. In step 2, a plunger 110 is pushed into the vessel which causes the first component 600 to be dispensed from the vessel 100 via an outlet 604. The second component 602 is trapped within the vessel by seal 106 and can be stored for use at a later time as shown in step 3. In step 4, the plunger 110 is partially withdrawn from the vessel 100 which draws the seal 106 from left to right. This causes the seal 106 to engage projections 108 provided on an internal wall of the vessel 100. A portion of the seal 106 is urged away from the internal wall of the vessel 100 causing channels to form between the seal 106 and the internal wall. This allows the second component 106 to enter the first chamber as shown in step 5. The second component is then dispensed from the vessel 100 via the outlet 604 by once again pushing the plunger into the vessel as in step 2.

FIG. 7A shows an embodiment of a vessel 700 in the form of a bottle/vial/cartridge comprising a screw cap 702. The vessel 700 also comprises a first chamber 704, a second chamber 706, a seal 106 and a projection 108. The cap 702 includes an actuator in the form of an elastic top portion 710 which can be depressed. Depression of the elastic portion 710 increases the pressure within the second chamber 706 and forces the seal 106 to engage the projections 108. Upon engagement of the seal 106 with the projections 108, the seal partially deforms and a channel is opened to provide communication between the first chamber 704 and the second chamber 706.

FIG. 7B shows a related embodiment of a vessel 700 in the form of a bottle/vial/cartridge comprising a screw cap 702. The vessel 700 comprises a first chamber 704, a second chamber 706, a seal 106 and a projection 108. A mechanical linkage 708 is provided between the elastic portion 710 and the seal 106. In this embodiment, depression of the elastic portion 710 is transmitted to the seal 106 via the linkage 708 causing the seal 106 to engage the projections 108. Upon engagement of the seal 106 with the projections 108, the seal partially deforms and a channel is opened to provide communication between the first chamber 704 and the second chamber 706.

Figure 8:
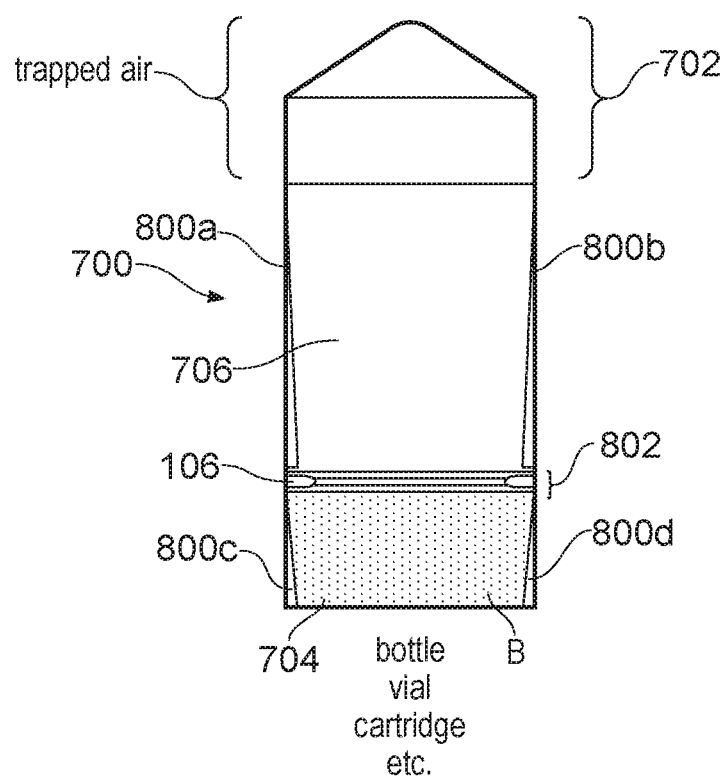
FIG. 8: a multi-chambered vessel configured to exclude air/oxygen from a chamber thereof.

FIG. 8 shows another embodiment of a vessel 700 in the form of a bottle/vial/cartridge comprising a screw cap 702. The cap 702 includes an actuator in the form of an elastic top portion which can be depressed. The vessel comprises a first chamber 704, a second chamber 706, and a seal 106. The first chamber 704 contains component B. In this embodiment, first 800a, second 800b, third 800c and fourth 800d projections are provided. The first 800a and second 800b projections are spaced circumferentially relative to one another and longitudinally relative to the third 800c and fourth 800d projections, which are in turn spaced circumferentially relative to one another. A gap 802, the length of which is at the thickness of the seal 106, separates the first 800a and second projections 800b from the third 800c and fourth projections 800c.

Figure 7:
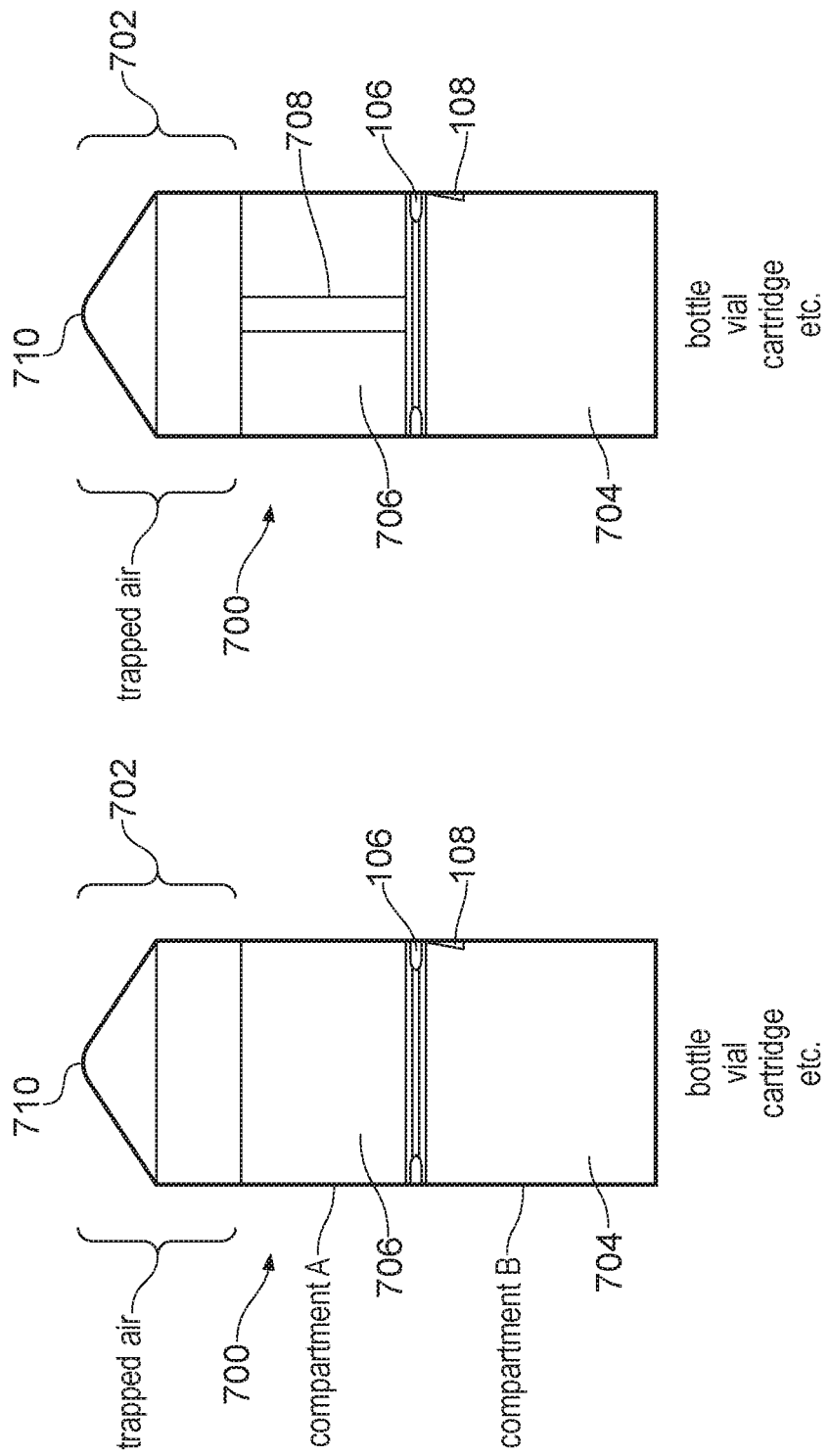
FIGS. 7A and 7B: a multi-chambered vessel in the form of a bottle comprising a screw cap.

The function of the third 800c and fourth 800d projections is to engage the seal 106 to open a channel through which component B can move from the first chamber 704 into the second chamber 706 in the manner described with reference to FIG. 7. In this embodiment, the third and fourth projections extend all the way to the base or end wall of the vessel 700. The seal 106 may therefore be moved right down to the base/end wall of the vessel, thereby forcing all of the contents of the first chamber 704 into the second chamber 706. Such a configuration may be applied to any type of vessel and is not limited to the specific embodiment of a vessel shown in this figure.

The first 800a and second 800b projections are provided to allow air/oxygen to be removed from the first chamber 704 during filling of the vessel. Such vessels may be provided to a user pre-filled and hence it is advantageous to remove or exclude oxygen/air from one or more of the chambers to increase shelf life. This can be achieved using the following steps.

First, component B is introduced into what will form the first chamber 704 of the vessel 700. Subsequently, the seal 106 is inserted into the vessel 700. This engages with the first 800a and second 800b projections such that one or more channels are present between the seal 106 and the internal wall of the vessel 700. The seal 106 is then forced longitudinally through the vessel 700 using the actuator (which in this embodiment is an elastic portion of the cap 702) along the first 800a and second 800b projections towards component B. Air/oxygen is forced out of the first chamber 704 through the channels by the movement of the seal 106. Eventually, the seal reaches the ends of the first 800a and second 800b projections and re-engages the internal wall of the vessel 700 at the gap 802 separating the first 800a and second 800b projections from the third 800c and fourth 800d projections. In this position (the position shown in FIG. 8), component B cannot move into the second chamber 706. The length of the projections and hence position of the gap 802 will be chosen according to the volume of component B to be stored in the first chamber 704 and the amount of air/oxygen which is to be permitted to remain in the first chamber 704. If air/oxygen is to be substantially excluded from the first chamber 704, the gap 802 may be positioned such that the seal contacts the surface of component B once it re-engages the wall of the vessel at the gap 802 as shown in FIG. 8.

When a user wishes to transfer component B into the second chamber 706, the seal 106 is engaged with the third 800c and fourth 800d projections. Alternatively, in certain embodiments, the seal 106 may be re-engaged with the first 800a and second 800b projections to open a channel through which component B may pass into the second chamber 706. In such embodiments, the third 800c and fourth 800d projections may be omitted.

FIGS. 9A-9E is a schematic illustration showing how gas can be removed from a chamber of a vessel. A vessel 900 has a proximal end 901 and a distal end 903. The vessel 900 comprises a proximal bypass zone 902 comprising first and second proximal projections 902a on an internal wall of the vessel. The vessel also includes a distal bypass zone 904 comprising first and second distal projections 904a on an internal wall of the vessel. The vessel 900 is partially filled with a first component 906 (FIG. 9A). A seal 908 is then inserted into the vessel 900 (FIG. 9B). The seal engages the proximal projections 902a thereby opening one or more channels between the internal wall of the vessel 900 and the seal 908 which bypass the seal 908. The seal 908 defines first 912 and second 910 chambers within the vessel (FIG. 9C). It will be appreciated that the relative sizes of the first and second chambers 912, 910, will change as the seal 908 moves though the vessel 900. As the seal 908 is moved towards the distal end 903 of the vessel 900, this action forces air trapped in the first chamber 912 passed the seal 908 via the channels and into the second chamber 910 (illustrated by the curved arrows in FIG. 9C). The seal 908 then disengages the proximal projections 902a and is positioned at a sealing position between the proximal bypass zone 902 and the distal bypass zone 904 (FIG. 9D). The proximal and distal bypass zones 902 and 904 respectively are separated by a distance d that is greater than or equal to the thickness of the seal 908. In this embodiment, the first component 906 is filled to the proximal end of the distal bypass zone 904, and d is equal to the thickness of the seal meaning that the seal 908 sits on the surface of the first component 906 and all air is excluded from the second chamber 912. A second component 914 is added into the vessel (FIG. 9D). Following this, a cap 916 may be used to close the opening in the proximal end of the vessel 901. As the seal 908 and the projections 902a are no longer engaged with each other, the channels are closed and therefore communication between the second chamber 910 and the first chamber 912 is prevented. The first component 906 and the second component 914 cannot contact each other while the seal 908 is at the sealing position. In order to contact the first component 906 with the second component 914, the seal is moved into the distal bypass zone 904 and engages the distal projections 904a thereby opening channels between the seal 908 and the vessel wall (FIG. 9E). As the seal 908 is moved further towards the distal end 903 of the vessel, the first component 906 is forced passed the seal 908 and into the second chamber 910 where it contacts the second component 914 (illustrated by the curved arrows in FIG. 9E). The mixed first and second components can be dispensed from the vessel 900 by removing the cap 916 (not shown).

FIG. 10 illustrates an alternative option to the step shown in FIG. 9E. Instead of moving the seal 908 into the distal bypass zone 904, the seal 908 is moved back into the proximal bypass zone 902. The seal 908 engages the proximal projections 902a, thereby opening channels between the seal 908 and the vessel wall. As the seal 908 is moved towards the proximal end 901 of the vessel 900, the second component 914 is forced passed the seal into the first chamber 912 via the channels and can contact the first component 906. This option may be preferred if the mixed components are to be dispensed via an opening at the distal end 903 of the vessel 900 (not shown).

Figure 11:
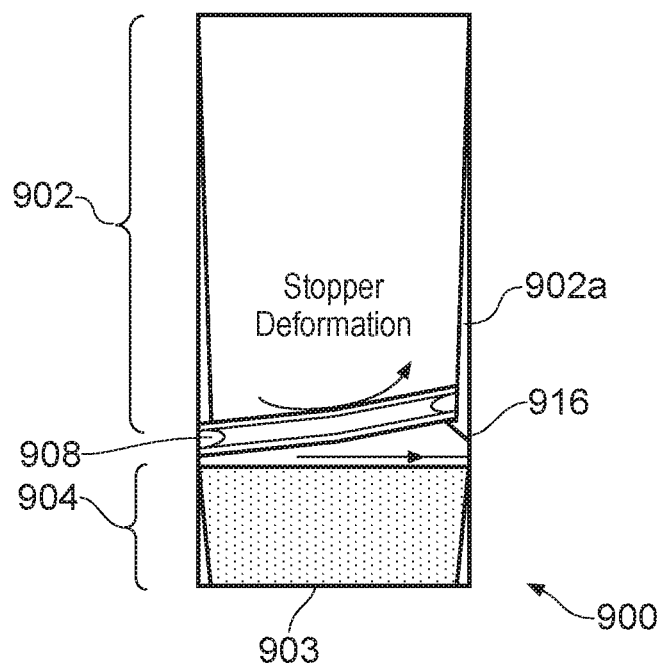
FIG. 11: a vessel comprising a proximal projection which includes a barb/hook.

FIG. 11 shows a vessel 900 comprising a proximal bypass zone 902 having first and second proximal projections 902a on an internal wall of the vessel. The vessel 900 also includes a distal bypass zone 904 comprising first and second distal projections 904a on an internal wall of the vessel. In this embodiment, a proximal projection 902a includes a barbed/hooked portion 916 at its distal end. The barbed/hooked portion 916 is adapted to catch a portion of the seal 908 as the seal moves towards the distal end 903 of the vessel 903, causing the seal to deform. This deformation improves fluid flow passed the seal 908.

Figure 12A:
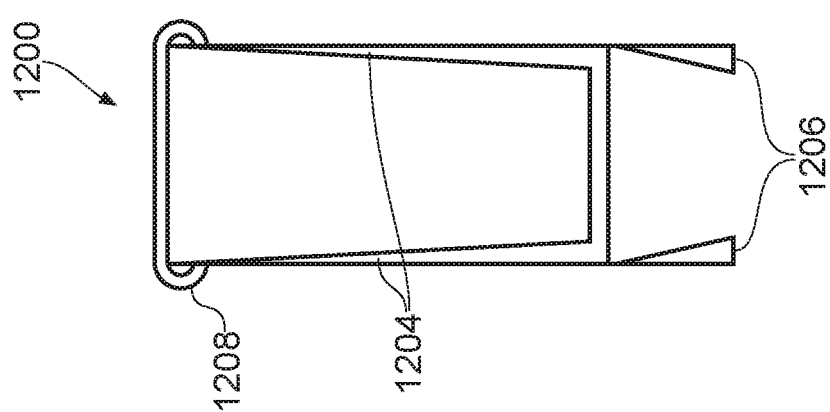
FIGS. 12A and 12B: a kit comprising proximal and distal projections and a view of the kit secured to a vessel.
Figure 12B:
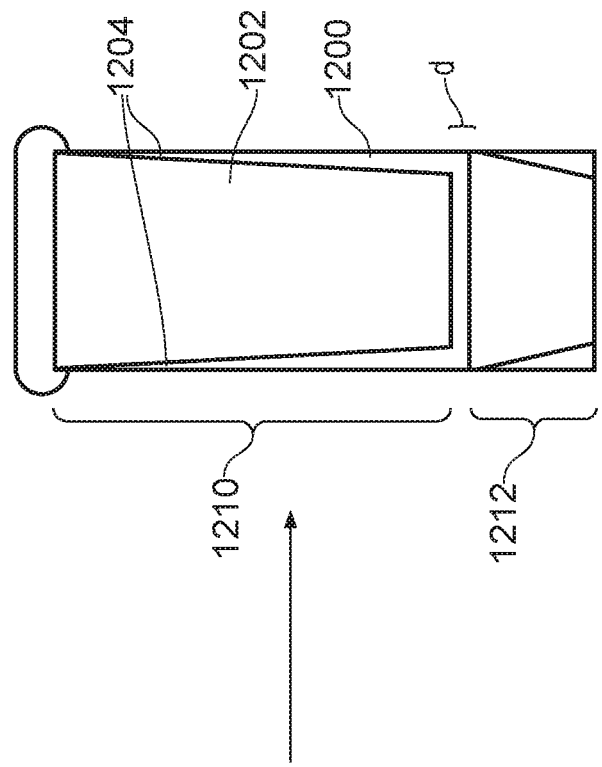

FIGS. 12A-B shows a side view of an embodiment of a kit 1200. The kit 1200 comprises proximal projections 1204 and distal projections 1206. The kit 1200 includes securing means 1208 that are configured to hook over the rim of a vessel 1202 and clip the kit to the vessel as illustrated in FIG. 12B. When the kit 1200 is fixed in the vessel 1202, the proximal projections 1204 define a proximal bypass zone 1210 and the distal projections 1206 define a distal bypass zone 1212. The proximal bypass zone 1210 is separated from the distal bypass zone 1212 by a distance d. This kit is configured for use with a seal that has a thickness that is less than or equal to the distance d.

Figure 13:
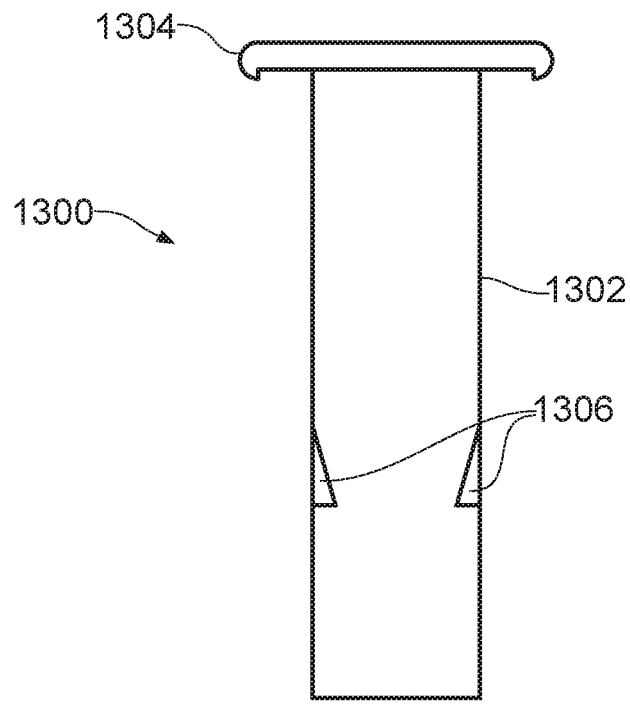
FIG. 13: a kit having an insert sleeve comprising projections on an internal wall thereof.

FIG. 13 shows a kit 1300 comprising an insert sleeve 1302 configured to fit tightly inside a vessel (not shown). The kit includes securing means 1304 adapted to secure the kit to the vessel. The insert sleeve includes projections 1306 on an internal wall thereof.

Figure 14A:
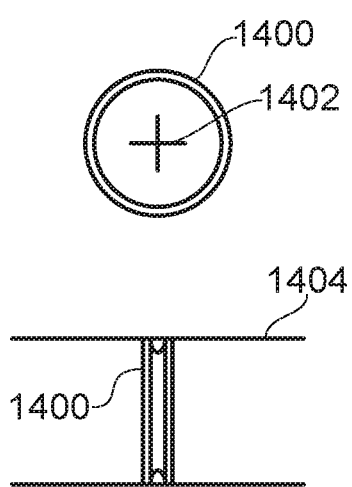
FIG. 14: a seal comprising a bypass slit.
Figure 14B:
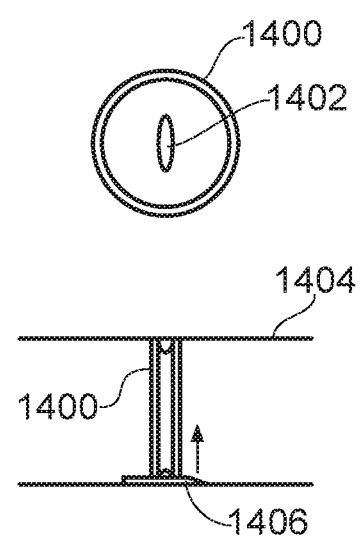

FIG. 14 shows a seal 1400 comprising a bypass slit 1402. When the seal 1400 is located in a sealing position within a vessel 1404 as shown in FIG. 13A (front and side views), the bypass slit 1402 is closed. When the seal 1400 engages a projection 1406, the seal 1400 partially deforms, thereby opening the bypass slit 1402 (as shown in FIG. 14B).

FIG. 15A shows a cross section of an insert sleeve 1500 for a vessel. The insert sleeve 1500 includes a bypass zone comprising a bypass channel 1502. FIG. 15B shows a vessel 1504 in the form of a syringe to which the insert sleeve 1500 has been fitted. A seal 1506 is provided within the vessel 1504. The insert sleeve 1500 includes a proximal sealing zone 1510, a distal sealing zone 1512 and a bypass zone 1508. When the seal 1506 is in either the proximal sealing zone 1510 or the distal sealing zone 1512, fluid cannot flow passed the seal 1506 because the cross section of the seal is substantially equal to the cross section of the proximal and distal sealing zones 1512, 1510. When the seal 1506 is in the bypass zone 1508 as shown in FIG. 15B, fluid can bypass the seal 1506 via the bypass channel 1502. The bypass zone 1508 has a larger cross section than the cross section of the seal 1506. The seal 1506 can be moved between zones using an actuator e.g. a piston 1514.

Example 1

Several proof of concept tests were carried out using single use plastic syringes having a variety of capacities.

In this example a low capacity syringe was chosen in order to simulate the single use prefilled syringes commonly used for the administration of intra-articular injections of hyaluronic acid in the joints for the treatment of Osteoarthritis. Moreover, such syringes (in combination with the liquid components tested) were considered to represent a "high difficulty" configuration (due to the narrow barrel) which could prove at the same time that the invention functions and is efficient across a wide range of applications and for use with other components and syringes.

A 2.5 ml syringe (PIC Solution of Artsana SPA Italy) single use, latex free, pthalates free, pyrogen free, ethylene oxide sterilised was identified as a suitable syringe for the test. The syringe had an inner barrel diameter of 9 mm and comprised a plunger which terminated in a seal. The plunger seal comprised pronounced annular portions having a diameter of 9.2 mm, between which were two furrows, the front furrow (the one closest to the conical terminus) having a "depth" of 1 mm. The length (side view) of the plunger seal was 5 mm excluding the 2 mm conical terminus.

A second seal (exactly the same as the plunger seal) was provided for the purpose of forming two chambers within the syringe such that two components could be stored separately (for example prior to administration). The chambers will be referred to as chamber A and chamber B, chamber B being closest to the plunger and chamber A being closest to the syringe's outlet.

Two individual projections each having a generally cylindrical cross section were fixed on the internal wall of the barrel. Each projection was tapered at both ends and had a maximum height of 0.9 mm extending into the barrel of the syringe. The second projection was provided on the opposite side of the inner wall to the first projection. The length of the projections was equal to that of the second seal (excluding its conical terminus) i.e. 5 mm.

The syringe was filled with 0.5 of water. The second seal was then inserted to confine the water to chamber B. The projections were situated in chamber A and it was confirmed that water could not pass into chamber A. The plunger was then depressed. This forced the second seal to engage the projections along the entire 5 mm length of the seal (with no significant resistance). This allowed water to pass into chamber A via two channels which had formed around the projections between the second seal and the internal wall of the barrel. It was surprisingly noticed that even one single projection was enough to create a channel or possibly two allowing the water to pass around the projection and enter chamber A.

Example 2

A second experiment was conducted using the syringe and protocol of Example 1 except that water was replaced with a high viscosity liquid component. The selected viscous liquid component was 1.5%.sodium hyaluronate in 0.2M sodium chloride with a measured zero shear viscosity of 530 Pas.

Again surprisingly, despite the high viscosity of the component, the test was successful and the sodium hyaluronate solution was able to pass into chamber A via channels formed around the projections.

Surprisingly both forward and backward movement (suction) of the plunger were found to be effective in causing engagement of the second seal and the projections leading to the formation of channels through which either of the components tested could pass. It is worth noting that the resistance in engaging and "riding" of the projections by the second seal in both cases was insignificant, while a minimal increase in resistance in both movements (forward and backward) was only observed the moment the conical terminus of the plunger itself had to ride the projections. A small deformation of the plunger (in the shape of the projection) was noticed for that reason after the experiment was completed. Adjustments of the various parameters (as described herein) can be made to avoid this if necessary.

The invention claimed is:

1. A vessel (700, 900) having a proximal end (901) and a distal end (903) and comprising
   a removable seal (106, 908) for defining a first chamber (704, 912) at the distal end (903) of the vessel and a second chamber (706, 910) at the proximal end (901) of the vessel (700, 900),
   a proximal bypass zone (902) comprising one or more proximal projections (800a, 800b, 902a) on an internal wall of the vessel (700, 900) or one or more proximal bypass channels (1502) on an internal wall of the vessel (700, 900),
   a distal bypass zone (904) comprising one or more distal projections (800c, 800d, 904a) on an internal wall of the vessel (700, 900), or one or more distal bypass channels (1502) on an internal wall of the vessel (700, 900),
   an opening at the proximal end (901) of the vessel (700, 900) for introducing a component into the vessel (700, 900), and
   an actuator configured to move the seal (106, 908) through the vessel (700, 900),
   wherein the proximal (800a, 800b, 902a) and distal projections (800c, 800d, 904a) are configured to urge a portion of the seal (106, 908) away from the internal wall of the vessel (700, 900) upon engagement with the seal (106, 908) thereby opening one or more channels (114) which bypass the seal (106, 908), and
   wherein the proximal and distal bypass channels are configured such that a proximal bypass zone comprising a proximal bypass channel and a distal bypass zone comprising a distal bypass channel each have a cross section that is greater than the cross section of the seal (106, 908), such that the seal (106, 908) cannot prevent communication between the first (704, 912) and second (706, 910) chambers when it is positioned in the proximal bypass zone (902) or in the distal bypass zone (904),
   wherein the proximal bypass zone (902) and the distal bypass zone (904) are arranged to allow fluid to bypass the seal (106, 908) are separated by a distance (802) that is greater than or equal to the thickness of the seal (106, 908),
   the proximal bypass zone (902) and seal (106, 908) being arranged to expel gas, that would otherwise be trapped in the first chamber (704, 912) between the seal (106, 908) and the distal end (903) of the vessel (700, 900), from the first chamber (704, 912) as the seal (106, 908) is moved through the proximal bypass zone (902) towards the distal end (903) of the vessel (700, 900), wherein the length of the proximal bypass zone (902) is selected according to the volume of a first component (906) to be contained within the first chamber (704, 912) such that the first component (906) can be stored in the first chamber (704, 912) in the absence of gas.

2. The vessel (700, 900) of claim 1, wherein the vessel (700, 900) comprises at least two circumferentially spaced proximal projections (800*a*, 800*b*, 902*a*) and/or at least two circumferentially spaced distal projections (800*c*, 800*d*, 904*a*).

3. The vessel (700, 900) of claim 1, wherein the one or more proximal projections (800*a*, 800*b*, 902*a*) extend to the proximal end (901) of the vessel (700, 900), and/or wherein the one or more distal projections (800*c*, 800*d*, 904*a*) extend to the distal end (903) of the vessel (700, 900).

4. The vessel (700, 900) of claim 1, wherein at least a portion of at least one projection tapers towards the proximal end (901) of the vessel (700, 900).

5. The vessel of claim 1, wherein at least one of the projections includes a barbed or hooked region towards a distal end of the projection, adapted to cause partial deformation of the seal (106, 908) as the seal (106, 908) passes over the barb or hook.

6. The vessel of claim 1, wherein the vessel (700, 900) has an opening at its proximal end (901) via which the seal (106, 908) is inserted into the vessel (700, 900) and/or via which gas can escape as the seal (106, 908) is moved through the vessel (700, 900).

7. The vessel (700, 900) of claim 1, wherein the actuator comprises a piston.

8. The vessel (700, 900) of claim 1, wherein the actuator is incorporated into a lid (702) configured to close an opening at the proximal end (901) of the vessel (700, 900).

9. The vessel (700, 900) of claim 8, wherein the actuator comprises a bulb or pump.

10. The vessel (700, 900) of claim 1, wherein at least one projection is generally rectangular, triangular, circular or trapezoidal in cross section.

11. The vessel (700, 900) of claim 1, wherein at least one projection comprises an opening (115) extending through an entire longitudinal axis of the projection.

12. The vessel (700, 900) of claim 1, wherein the vessel (700, 900) is a syringe or a vial.

13. The vessel (700, 900) of claim 1, wherein the seal (106, 908) includes a bypass slit (1402) that is adapted to open when the seal (106, 908) engages a projection and close when the seal (106, 908) disengages the projection.

14. The vessel (700, 900) of claim 1, wherein the distal bypass zone (904) extends to the distal end (903) of the vessel (700, 900) such that the seal (106, 908) can be used to force the entire contents of the first chamber (704, 912) into the second chamber (706, 910) by moving the seal (106, 908) to the distal end (903) of the vessel (700, 900).

* * * * *